US006447293B1

(12) United States Patent
Sokol et al.

(10) Patent No.: US 6,447,293 B1
(45) Date of Patent: Sep. 10, 2002

(54) DRIVE MECHANISM FOR INTERPROXIMAL FLOSSING DEVICE

(75) Inventors: Gary Sokol, Niwot; Cliff Snyder, Fort Collins, both of CO (US)

(73) Assignee: Water Pik, Inc., Fort Collins, CO (US)

( * ) Notice: Subject to any disclaimer, the term of this patent is extended or adjusted under 35 U.S.C. 154(b) by 0 days.

(21) Appl. No.: 09/636,488

(22) Filed: Aug. 10, 2000

Related U.S. Application Data

(60) Provisional application No. 60/148,915, filed on Aug. 13, 1999.

(51) Int. Cl.[7] .............................................. A61C 15/00
(52) U.S. Cl. ......................... 433/118; 132/322; 433/122
(58) Field of Search .................. 433/118, 122, 433/124, 128; 132/322, 329; 15/167.1

(56) References Cited

U.S. PATENT DOCUMENTS

| 1,355,037 A | 10/1920 | Dziuk |
| 1,703,642 A | 2/1929 | Sticht |
| 2,016,597 A | 10/1935 | Drake |
| 2,931,371 A | 4/1960 | Petitta |
| 3,106,216 A | 10/1963 | Kirby |
| 3,270,416 A | 9/1966 | Massa |
| 3,335,443 A | 8/1967 | Parisi et al. |
| 3,375,820 A | 4/1968 | Kuris et al. |
| 3,472,045 A | 10/1969 | Nelsen et al. |
| 3,472,247 A | 10/1969 | Borsum et al. |
| 3,474,799 A | 10/1969 | Cappello |
| 3,552,022 A | 1/1971 | Axelsson |
| 3,559,292 A | 2/1971 | Weissman |
| 3,563,233 A | 2/1971 | Bodine |
| 3,588,936 A | 6/1971 | Duve |
| 3,660,902 A | 5/1972 | Axelsson |
| 3,672,378 A | 6/1972 | Silverman |
| 3,759,274 A | 9/1973 | Warner |
| 3,760,799 A | 9/1973 | Crowson |
| 3,809,977 A | 5/1974 | Balamuth et al. |
| 3,831,611 A | 8/1974 | Hendricks |
| 3,902,510 A | 9/1975 | Roth |
| 3,903,601 A | 9/1975 | Anderson et al. |

(List continued on next page.)

FOREIGN PATENT DOCUMENTS

| DE | 243224 | 4/1910 |
| DE | 17 66 651 C1 | 12/1981 |
| DE | 3431481 | 2/1986 |
| DE | 8626725 | 5/1987 |
| DE | 37 36 308 A1 | 7/1989 |
| DE | 41 42 404 C2 | 7/1991 |
| DE | 42 23 195 A1 | 1/1994 |
| DE | 42 23 196 A1 | 1/1994 |
| DE | 42 26 659 A1 | 2/1994 |
| DE | 43 09 078 A1 | 9/1994 |
| DE | 297 15 234 U1 | 12/1997 |
| EP | 0 354 352 | 2/1990 |
| EP | 0 661 025 B1 | 7/1995 |
| FR | 429447 | 9/1911 |
| WO | WO 94/04093 | 3/1994 |
| WO | WO 95/02375 | 1/1995 |

OTHER PUBLICATIONS

Sonex International: Brushing with the Ultima—The World's Only Dual–Frequency Ultrasonic Toothbrush, Jul. 28, 1999, published at Sonipic.com.

Primary Examiner—John J. Wilson
Assistant Examiner—Melba Bumgarner
(74) Attorney, Agent, or Firm—Dorsey & Whitney LLP

(57) ABSTRACT

An interproximal flossing device including a link member that isolates lateral from vertical rotational movement to transfer only translatory arcuate movement. This is done by the combination of a hinge and pivot structure. A tip attachment structure is also included for secure placement of the tip on the link member, and allows easy removal and replacement. A tip member removal structure is also included to allow for easy removal of the tip member from the link member.

4 Claims, 19 Drawing Sheets

U.S. PATENT DOCUMENTS

| | | | |
|---|---|---|---|
| 3,967,617 A | 7/1976 | Krolik | |
| 3,978,852 A | 9/1976 | Annoni | |
| 3,980,906 A | 9/1976 | Kuris et al. | |
| 4,004,344 A | 1/1977 | Gold et al. | |
| 4,005,722 A | 2/1977 | Bragg | |
| 4,008,728 A | 2/1977 | Sanchez | |
| 4,019,522 A | 4/1977 | Elbreder | |
| 4,048,723 A | 9/1977 | Thorup | |
| 4,064,883 A | 12/1977 | Oldham | |
| 4,133,339 A | 1/1979 | Naslund | |
| 4,192,035 A | 3/1980 | Kuris | |
| 4,205,664 A | 6/1980 | Baccialon | |
| 4,219,619 A | 8/1980 | Zarow | |
| 4,235,253 A | 11/1980 | Moore | |
| RE30,536 E | 3/1981 | Perdreaux, Jr. | |
| 4,289,486 A | 9/1981 | Sargeant | |
| 4,307,740 A | 12/1981 | Florindez et al. | |
| 4,319,377 A | 3/1982 | Tarrson et al. | |
| 4,319,595 A | 3/1982 | Ulrich | |
| 4,326,547 A | 4/1982 | Verplank | |
| 4,326,548 A | 4/1982 | Wagner | |
| 4,333,197 A | 6/1982 | Kuris | |
| D265,515 S | 7/1982 | Levine | |
| 4,338,957 A | 7/1982 | Meibauer | |
| 4,347,839 A | 9/1982 | Youngclaus, Jr. | |
| 4,397,327 A | 8/1983 | Hadary | |
| D272,565 S | 2/1984 | Levine | |
| 4,434,806 A | 3/1984 | Givens | |
| 4,458,702 A | 7/1984 | Grollimund | |
| 4,505,678 A | 3/1985 | Andersson | |
| 4,576,190 A | 3/1986 | Youssef | |
| 4,577,649 A | 3/1986 | Shimenkov | |
| 4,605,025 A | 8/1986 | McSpadden | |
| 4,608,019 A | 8/1986 | Kumabe et al. | 433/118 |
| 4,617,718 A | 10/1986 | Andersson | |
| 4,634,376 A | 1/1987 | Mossle et al. | 433/29 |
| 4,787,847 A | 11/1988 | Martin et al. | 433/119 |
| 4,791,940 A | 12/1988 | Hirshfeld et al. | 128/776 |
| 4,811,445 A | 3/1989 | Lagieski et al. | 15/104.94 |
| 4,820,153 A | 4/1989 | Romhild et al. | 433/118 |
| 4,820,154 A | 4/1989 | Romhild et al. | 433/128 |
| 4,832,063 A | 5/1989 | Smole | 132/329 |
| 4,913,133 A | 4/1990 | Tichy | 128/62 A |
| 4,922,936 A | 5/1990 | Buzzi et al. | 132/321 |
| 4,995,403 A | 2/1991 | Beckman et al. | 128/776 |
| 5,000,684 A | 3/1991 | Odrich | 433/125 |
| 5,002,487 A | 3/1991 | Tichy | 433/722 |
| 5,016,660 A | 5/1991 | Boggs | 132/322 |
| 5,050,625 A | 9/1991 | Siekmann | 132/323 |
| 5,067,223 A | 11/1991 | Bruno | 29/426.5 |
| 5,069,621 A | 12/1991 | Paradis | 433/147 |
| 5,071,348 A | 12/1991 | Woog | 433/118 |
| 5,094,256 A | 3/1992 | Barth | 132/322 |
| 5,100,321 A | 3/1992 | Coss et al. | 433/118 |
| 5,123,841 A | 6/1992 | Millner | 433/125 |
| 5,125,837 A | 6/1992 | Warrin et al. | 433/125 |
| 5,133,661 A | 7/1992 | Euvrard | 433/120 |
| 5,138,733 A | 8/1992 | Bock | 15/22.1 |
| 5,169,313 A | 12/1992 | Kline | 433/143 |
| 5,170,809 A | 12/1992 | Imai et al. | 132/322 |
| 5,174,314 A | 12/1992 | Charatan | 132/328 |
| 5,183,063 A | 2/1993 | Ringle et al. | 132/321 |
| 5,224,500 A | 7/1993 | Stella | 132/322 |
| 5,236,358 A | 8/1993 | Sieffert | 433/119 |
| 5,247,716 A | 9/1993 | Bock | 15/22.1 |
| 5,261,430 A * | 11/1993 | Mochel | 132/322 |
| 5,293,886 A | 3/1994 | Czapor | 132/329 |
| 5,323,796 A | 6/1994 | Urso | 132/322 |
| 5,369,831 A | 12/1994 | Bock | 15/22.1 |
| 5,393,229 A | 2/1995 | Ram | 433/118 |
| 5,406,965 A | 4/1995 | Levine | 132/323 |
| 5,411,041 A | 5/1995 | Ritter | 132/322 |
| 5,419,346 A | 5/1995 | Tipp | 132/329 |
| 5,419,703 A | 5/1995 | Warrin et al. | 433/216 |
| 5,482,466 A | 1/1996 | Haynes | 132/322 |
| 5,496,256 A | 3/1996 | Bock et al. | 601/2 |
| D370,125 S | 5/1996 | Craft et al. | D4/101 |
| 5,546,624 A | 8/1996 | Bock | 15/22.1 |
| 5,573,020 A | 11/1996 | Robinson | 132/322 |
| 5,579,786 A | 12/1996 | Wolk et al. | 132/322 |
| 5,606,984 A | 3/1997 | Gao | 132/325 |
| 5,618,275 A | 4/1997 | Bock | 604/290 |
| 5,700,146 A | 12/1997 | Kucar | 433/82 |
| 5,709,233 A | 1/1998 | Boland et al. | 132/322 |
| 5,718,667 A | 2/1998 | Sugimoto et al. | 601/139 |
| 5,738,575 A | 4/1998 | Bock | 433/216 |
| 5,787,908 A | 8/1998 | Robinson | 132/322 |
| 5,827,064 A | 10/1998 | Bock | 433/216 |
| 5,855,216 A | 1/1999 | Robinson | 132/322 |
| 5,896,615 A | 4/1999 | Zaksenberg | 15/167.1 |
| 5,899,693 A | 5/1999 | Himeno et al. | 433/119 |
| 5,927,300 A | 7/1999 | Boland et al. | 132/322 |
| 5,931,170 A | 8/1999 | Wu | 132/322 |
| 5,944,033 A | 8/1999 | Robinson | 132/322 |
| 6,095,811 A | 8/2000 | Stearns | 433/29 |

* cited by examiner

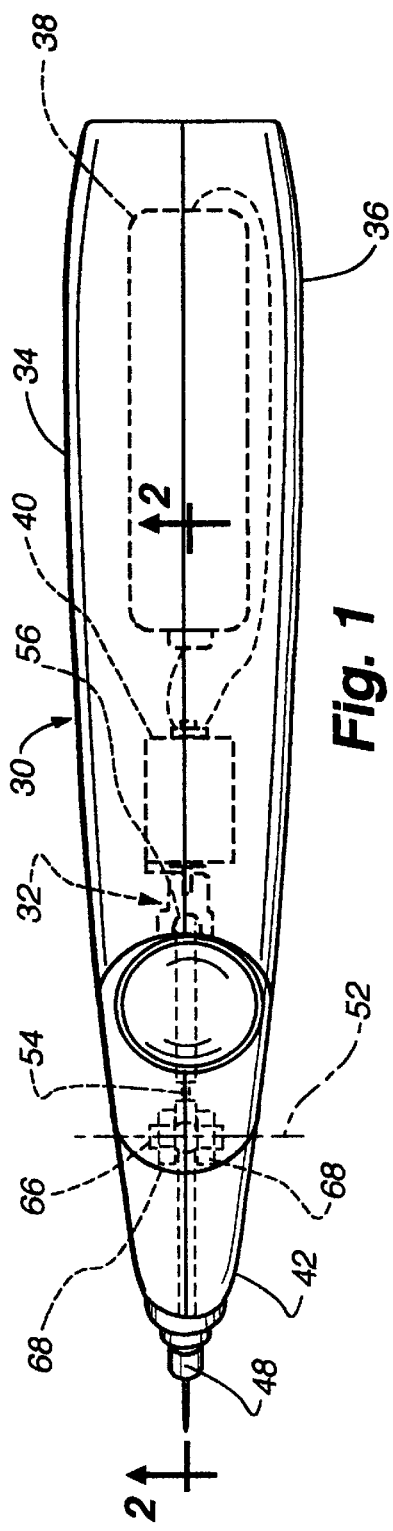
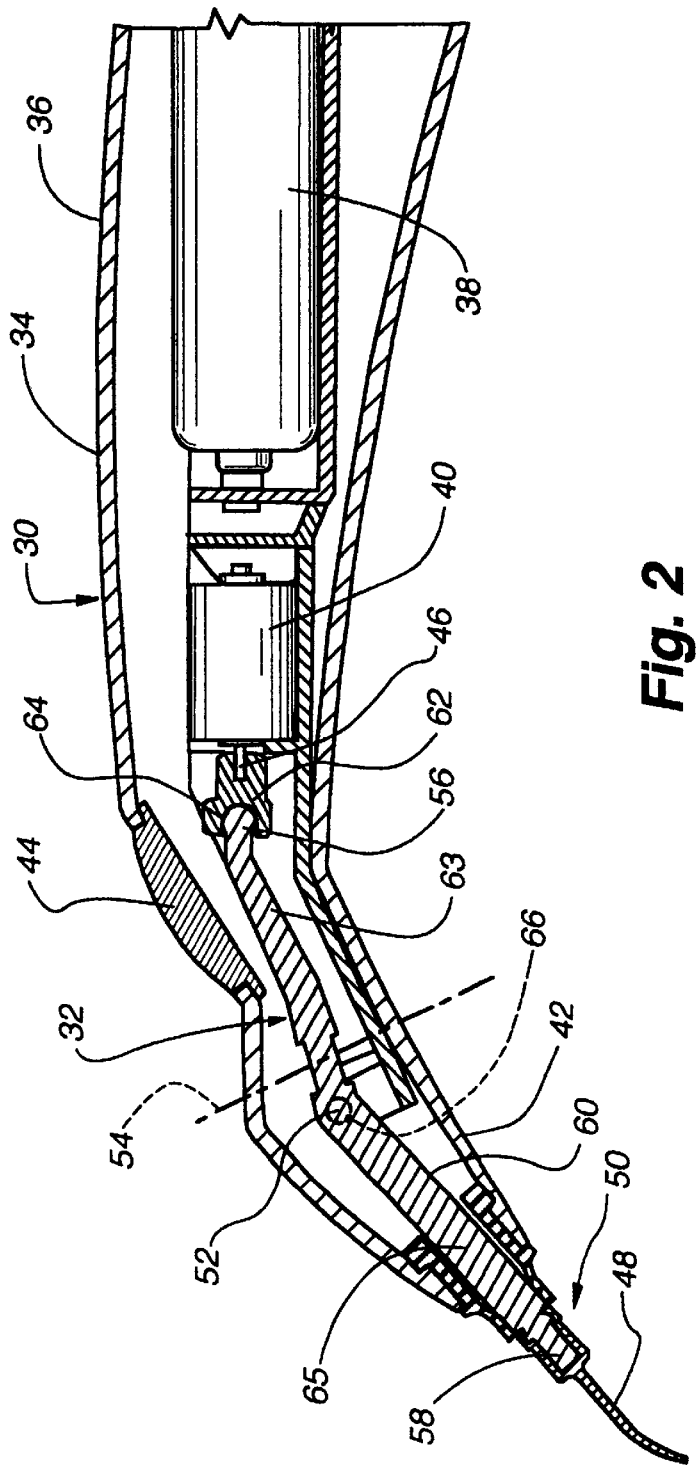
Fig. 1
Fig. 2

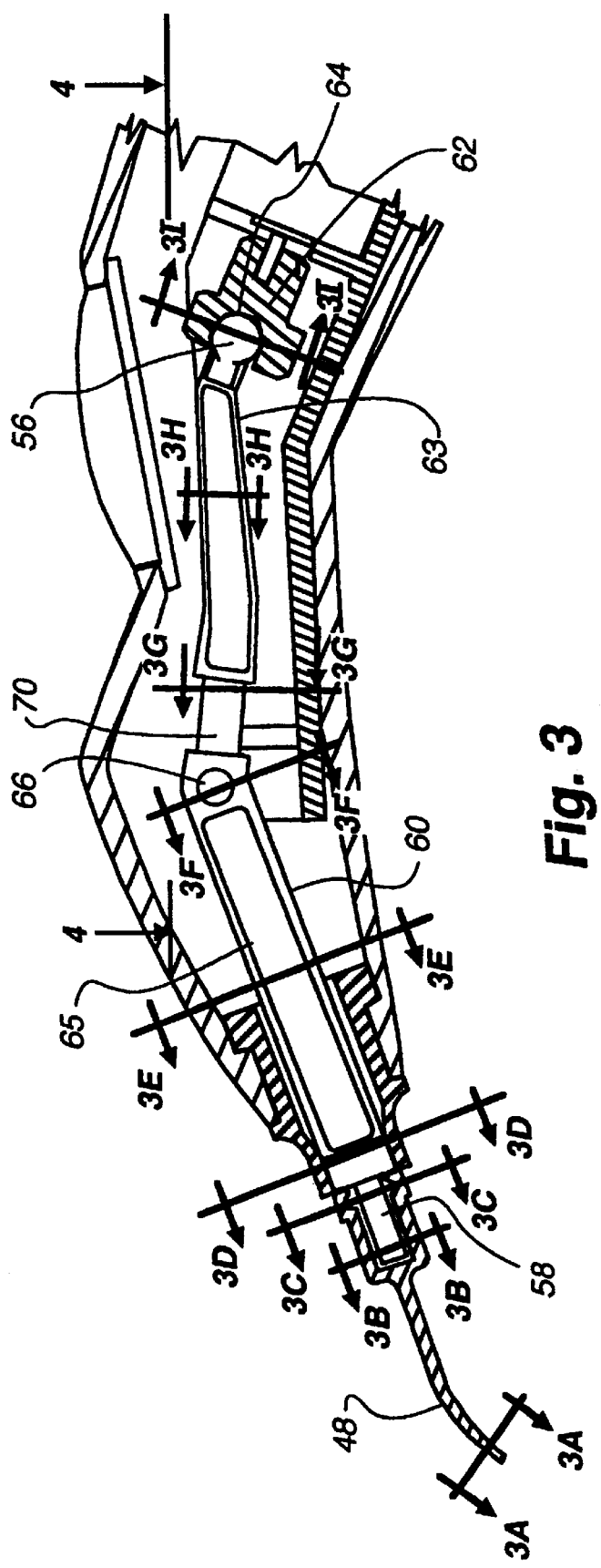
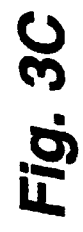
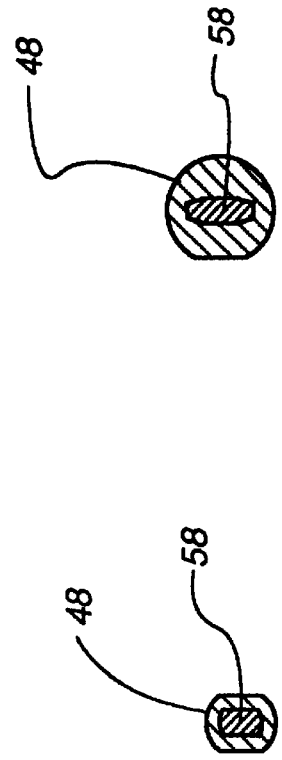
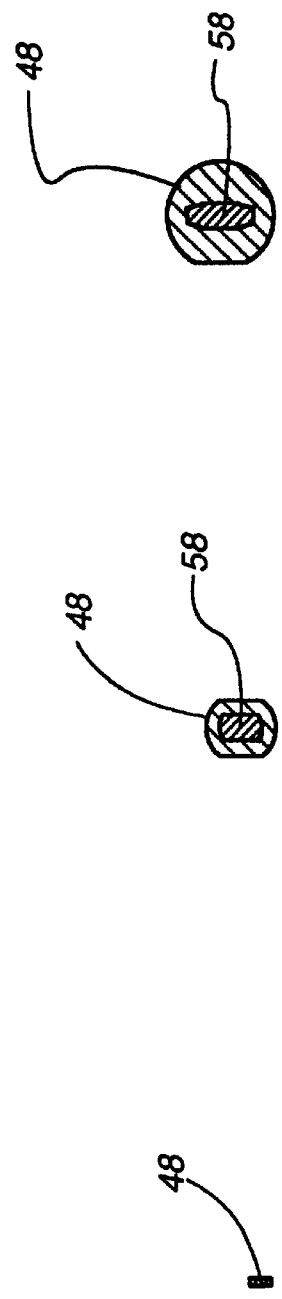
Fig. 3
Fig. 3A
Fig. 3B
Fig. 3C

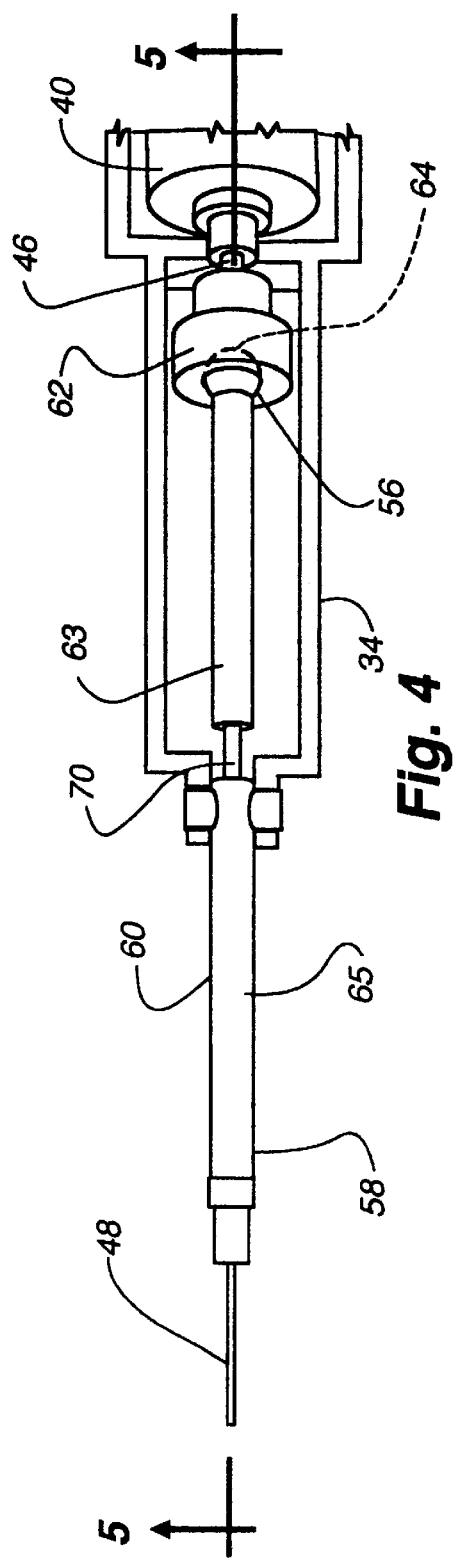
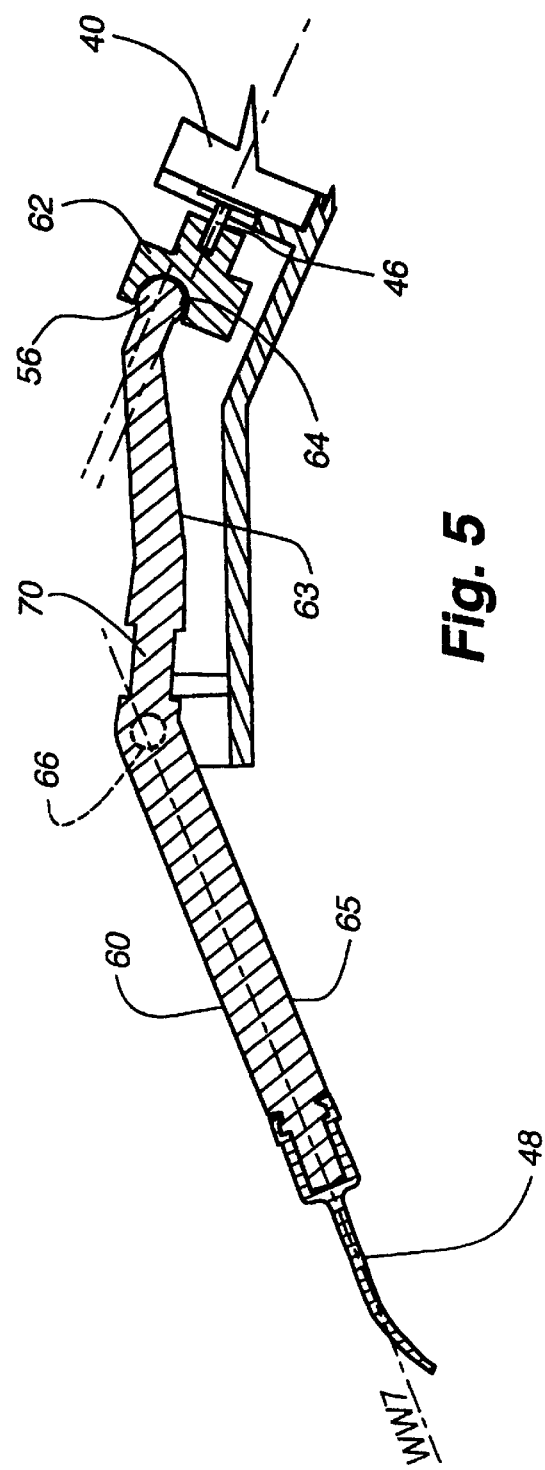

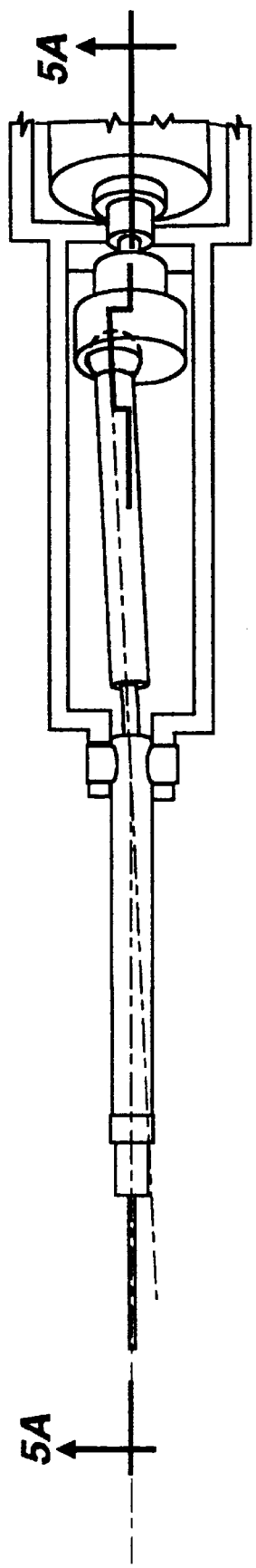
Fig. 4A
Fig. 4A'
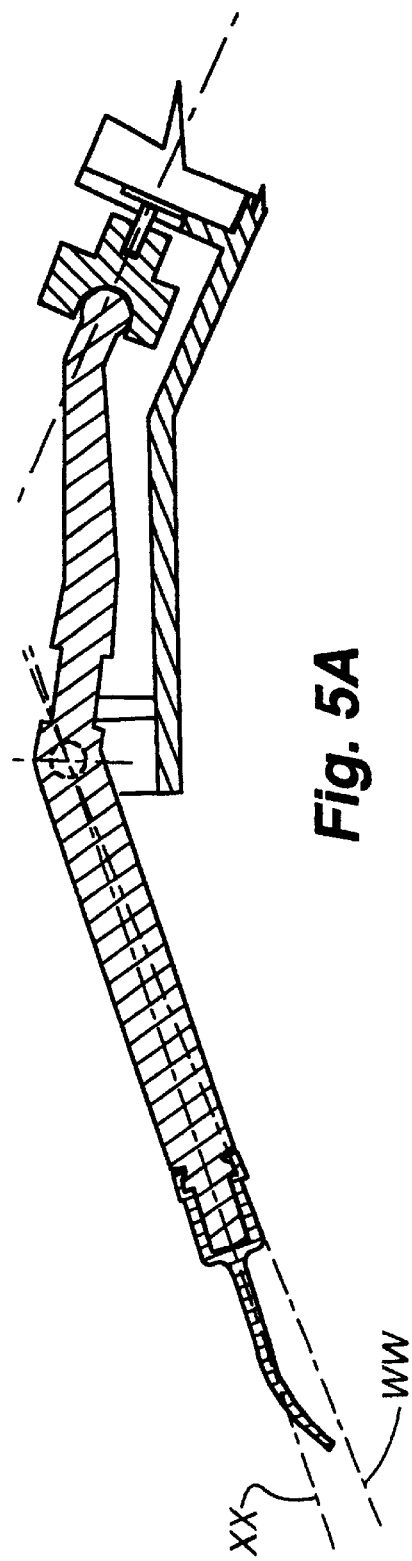
Fig. 5A

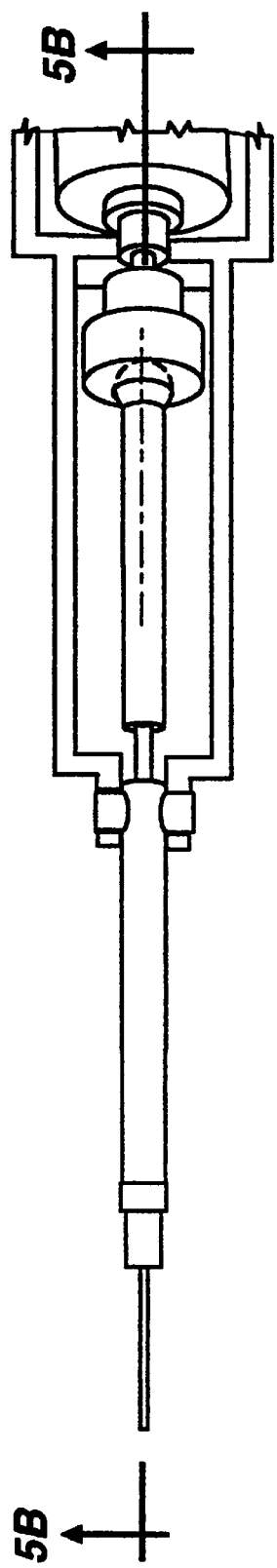
Fig. 4B
Fig. 4B'
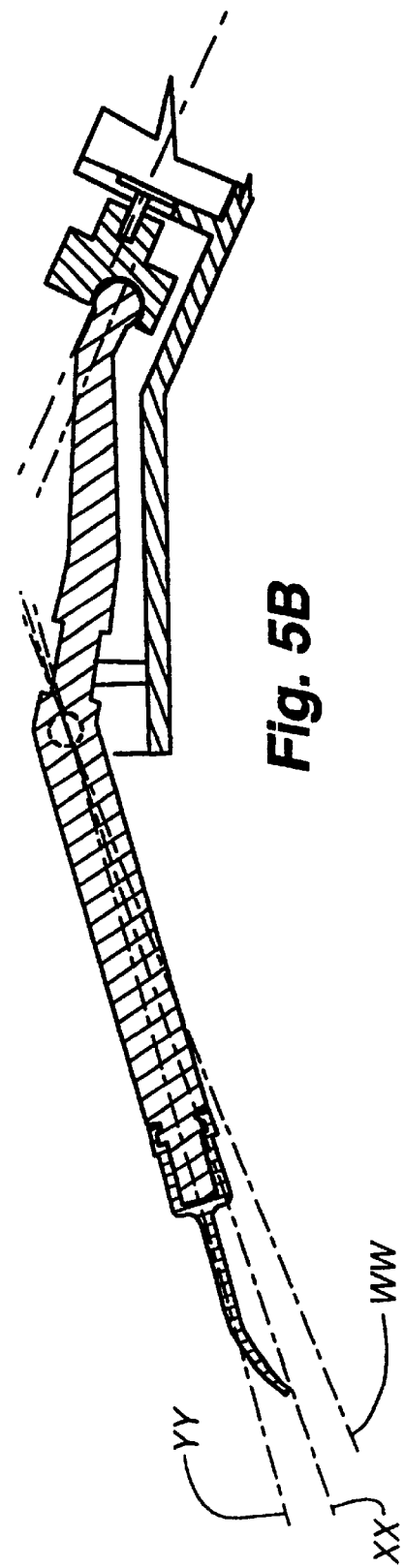
Fig. 5B

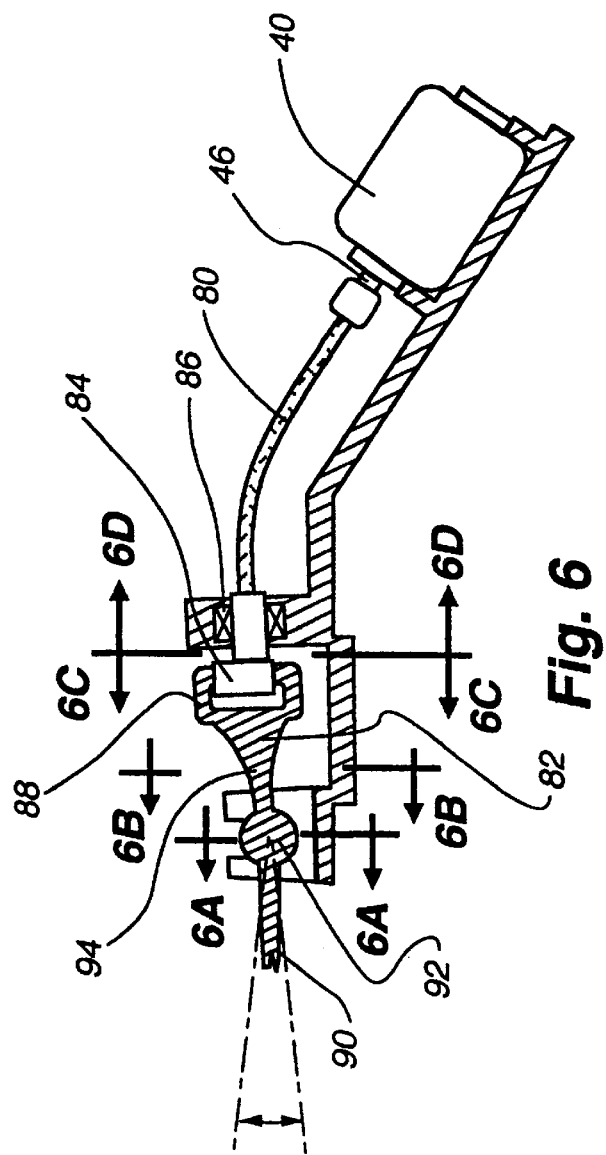
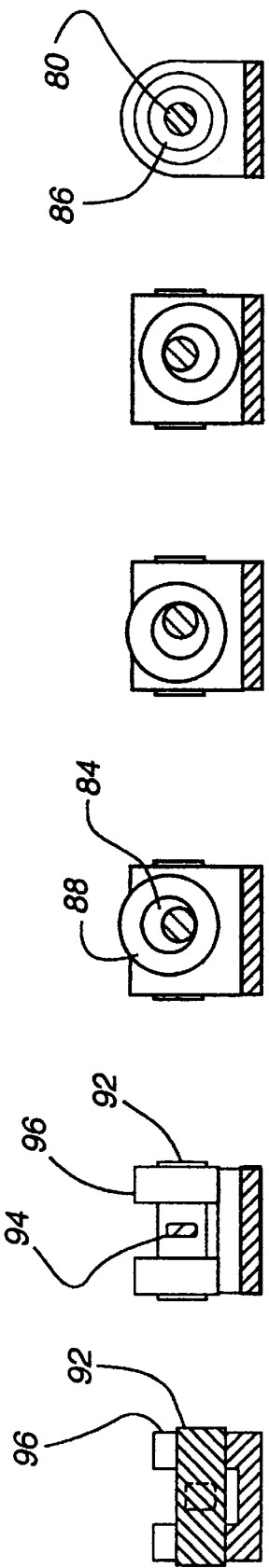

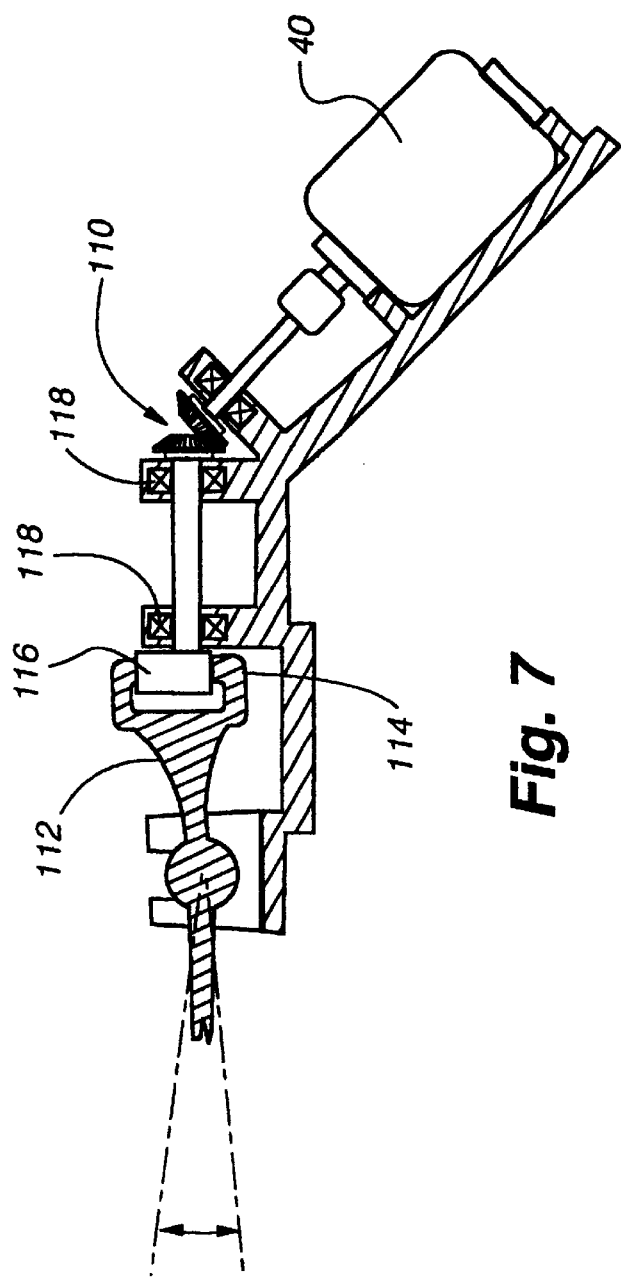
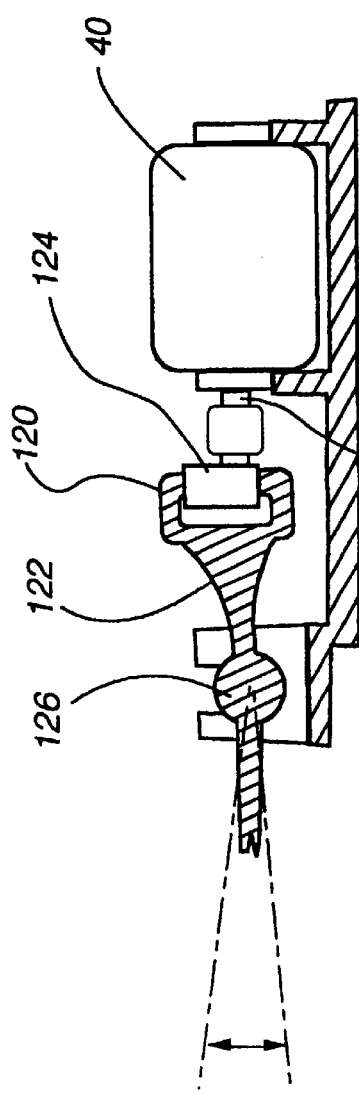
Fig. 7
Fig. 8

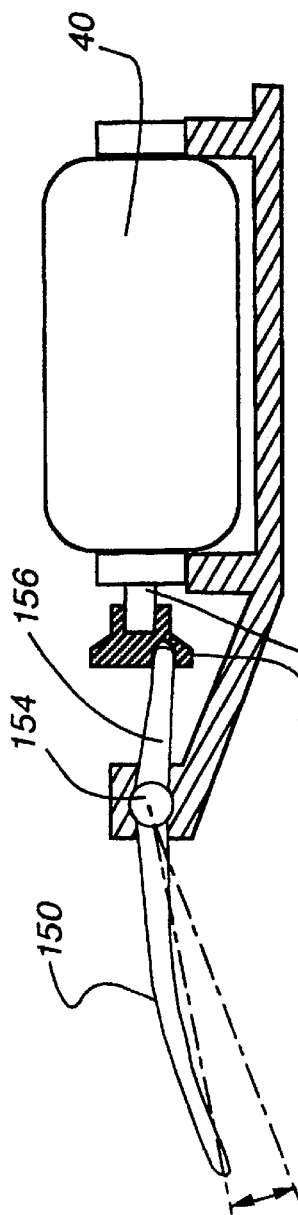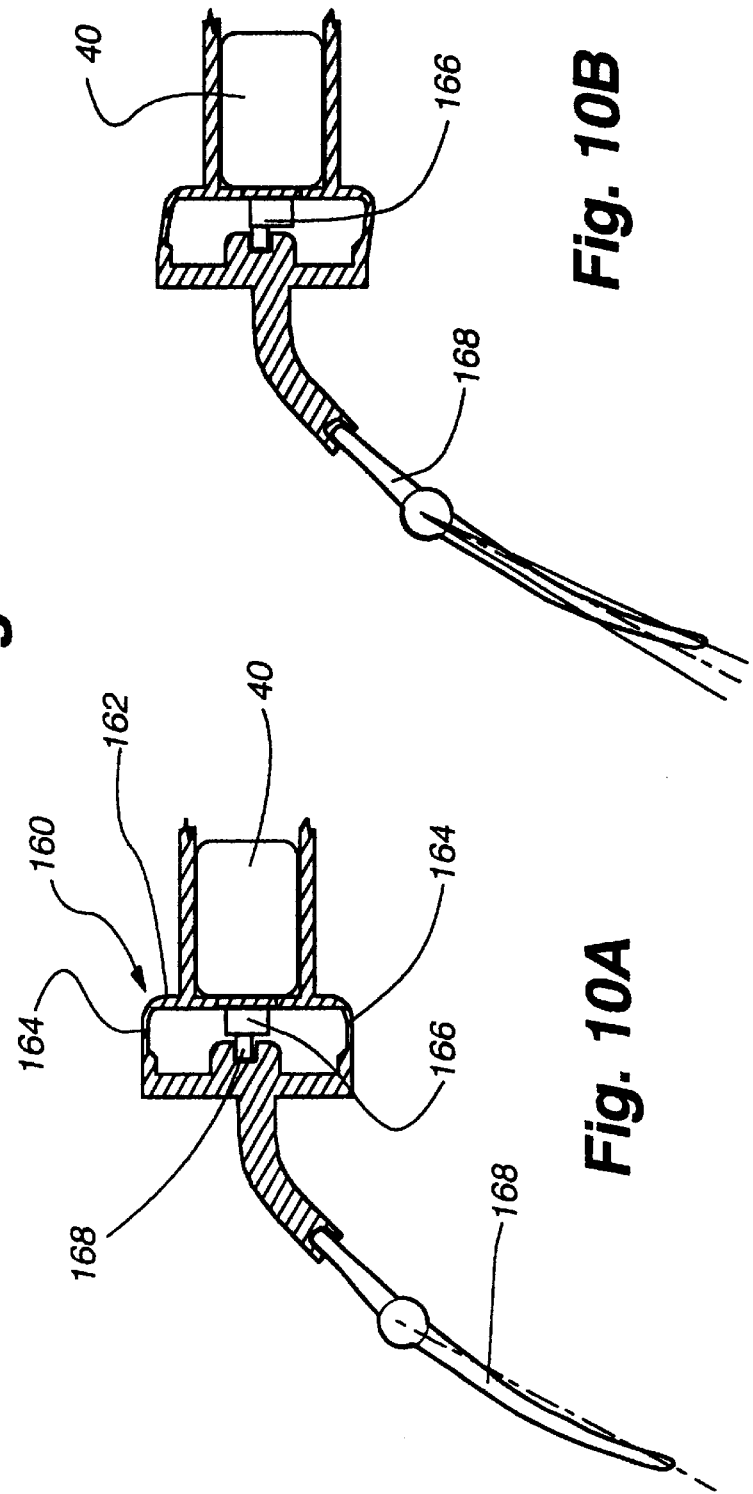

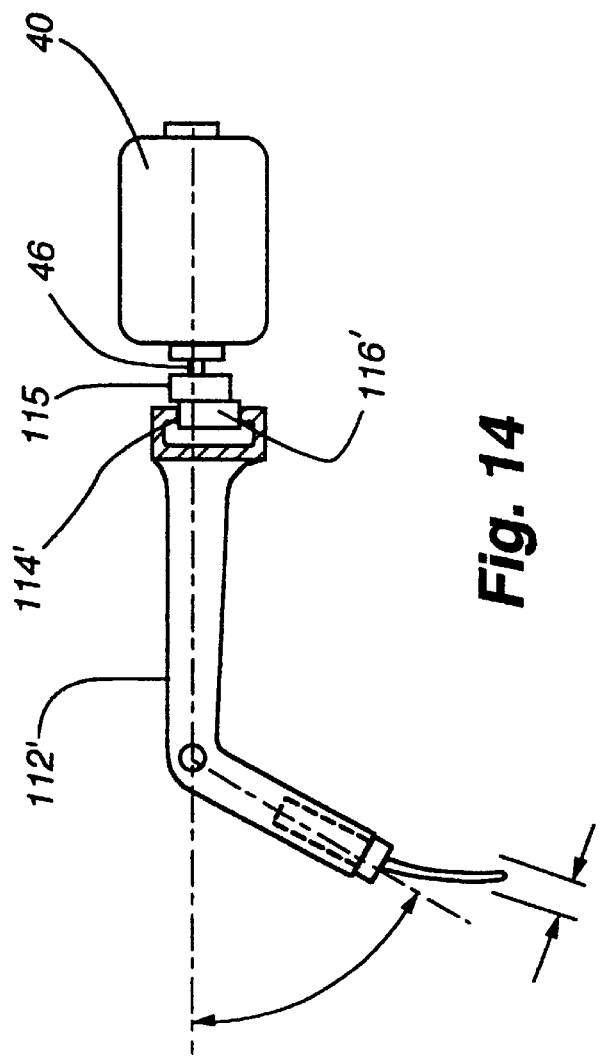
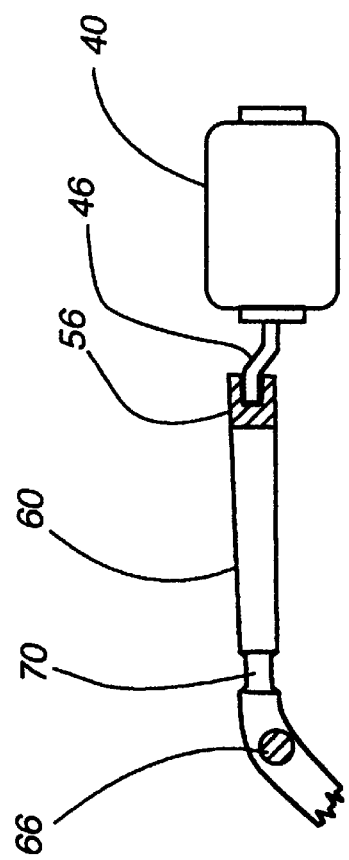

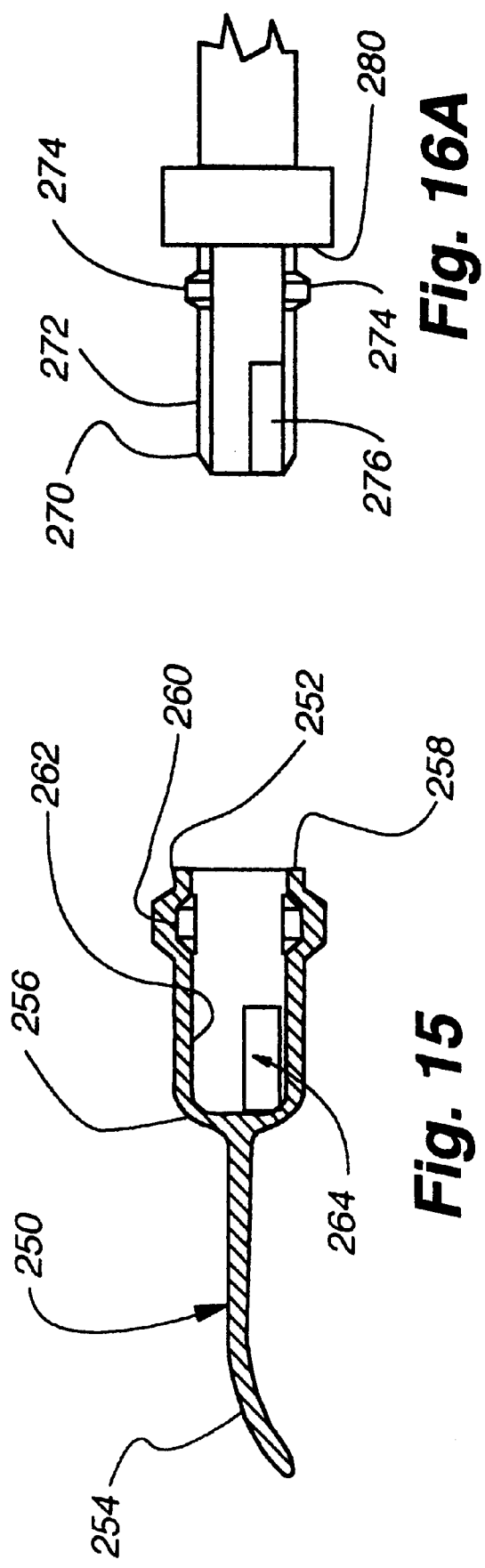
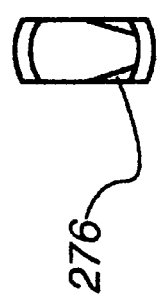

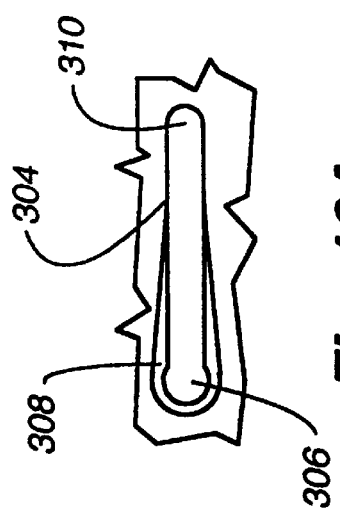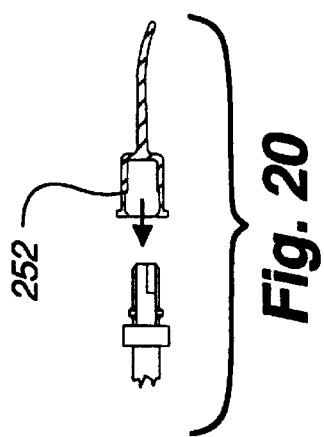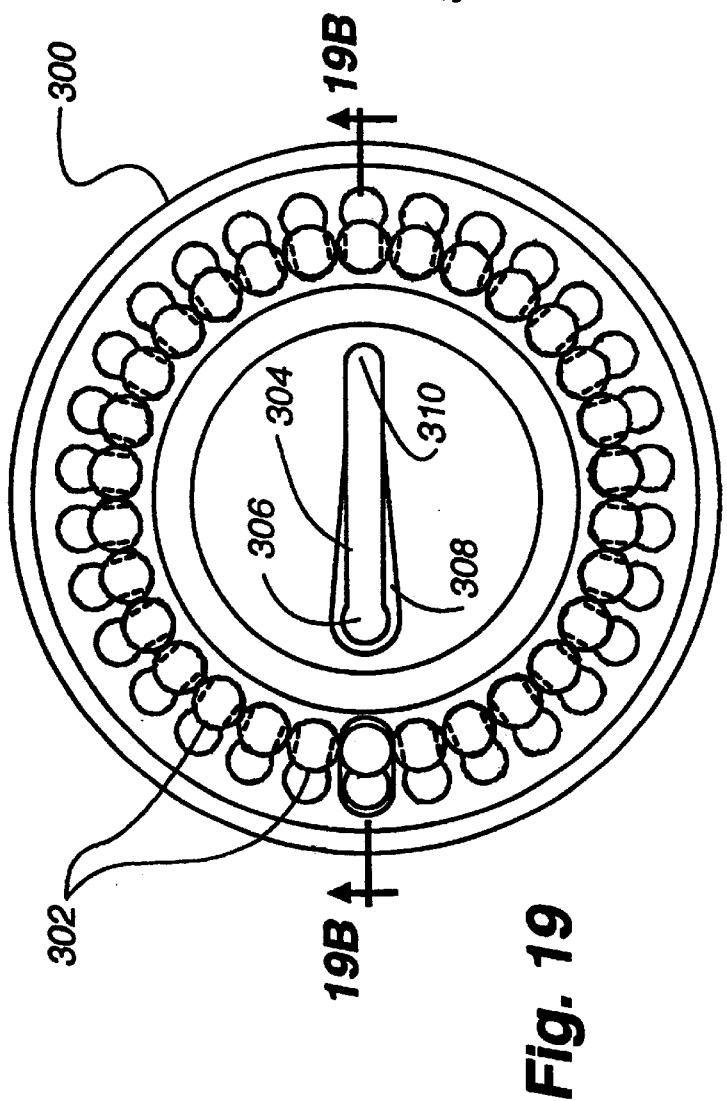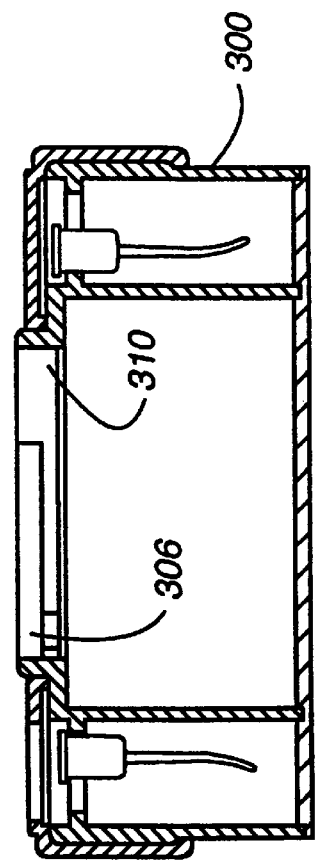

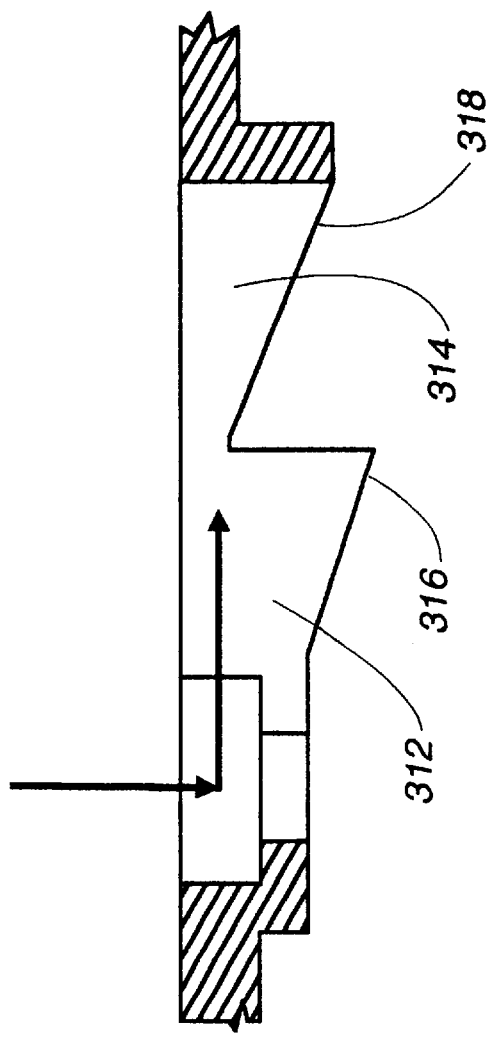
Fig. 22
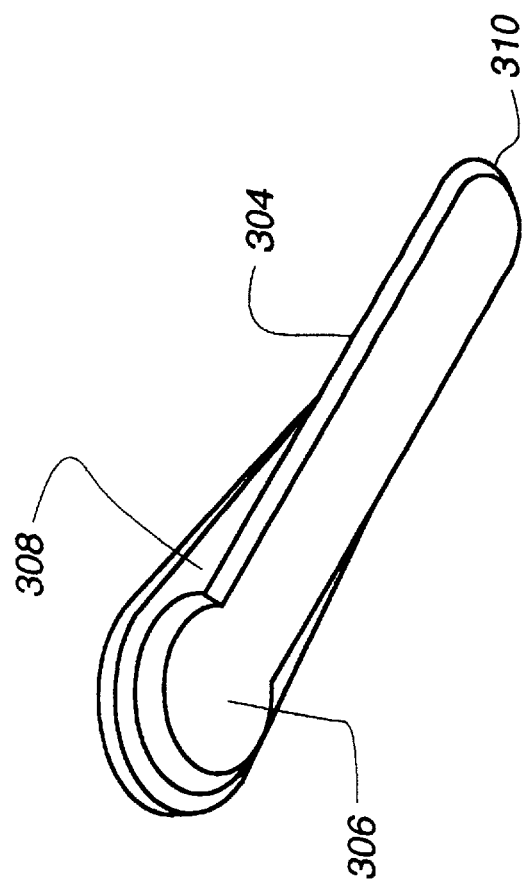
Fig. 19A1 ism for an interproximal flosser having an electric motor
DRIVE MECHANISM FOR INTERPROXIMAL FLOSSING DEVICE This application claims benefit of provisional application No. 60/148,915, filed Aug. 13, 1999.

FIELD OF THE INVENTION

This invention relates to interproximal flossing devices, and more particularly to the drive mechanisms for interproximal flossing devices and the tip attachment structure associated therewith.

BACKGROUND OF THE INVENTION

Available interproximal flossers employ a variety of tip movements to effect cleaning interproximal spaces formed between teeth. The tip movements typically include orbital, rotational, or linear movement. Rotational movement is typically created by a direct linkage between the tip and the drive shaft of a motor mounted in the handle. As the drive shaft rotates, the linkage and tip also rotate accordingly. Typically the rotation occurs in one direction, but can also be rotary oscillation. Rotation also occurs where the tip does not rotate about its longitudinal axis, but instead rotates about an axis offset from but generally parallel to the longitudinal axis of the tip. This Orbital tip movement is often created by using an off-center weight attached to the drive shaft of an electric motor mounted in the handle, which causes the entire device to move in an orbital manner in response to the off-center rotation of the weight. Orbital movement can be considered a subset of rotational movement because the tip rotates by moving along the orbital path.

Linear movement typically requires a linkage that converts the rotational movement of the motor drive shaft into linear oscillating movement at the tip. Oftentimes this structure for converting rotational to linear movement requires an offset cam surface mounted on the shaft of the motor with an end of the linkage attached thereto to follow the eccentric as it rotates. The end of the shaft is generally loosely engaged with the offset cam surface so that the shaft only moves in a direction to create linear motion at the tip end. In the linkage used to convert rotational movement to linear movement, there can be inefficiencies due to linkage connections (such as being loosely engaged), and difficulty in quietly connecting the linkage to the motor to avoid the creation of annoying sounds, due to loose connections, when the motor operates.

In addition, the tip connection structure typically used in interproximal flossing devices utilizes simple friction to attach the tip to the active end of the drive train. This type of connection is not secure, and can wear out and be less effective as the device is used.

It is with the above limitations of the presently available interproximal flossers that the invention described and claimed herein was developed.

SUMMARY OF THE INVENTION

The instant invention relates to a interproximal flossing device, and more particularly to the drive mechanism used in the device to create linear movement of the flossing tip. The interproximal flossing device of the present invention includes a link member that isolates lateral from vertical rotational movement to transfer only translatory arcuate movement. This is done by the combination of a hinge and pivot structure. A tip attachment structure is also included for secure placement of the tip on the link member, and allows easy removal and replacement. A tip member removal structure is also included to allow for easy removal of the tip member from the link member.

In one aspect of the invention, it includes a drive mechanism for an interproximal flosser having an electric motor with a rotating drive shaft, the drive mechanism comprising a link member having a first portion and a second portion, the first portion having a first end for attachment to the drive shaft in an off-center manner, and a second portion having a second end for receiving a tip member; a laterally-extending pivot axis formed on the link member; and a resiliently flexible hinge portion having a vertical bending axis formed on the link member. When the drive shaft rotates, the first end of the link member is rotated off-center from the drive shaft, creating vertical, lateral, and a combination of vertical and lateral movement, and the hinge isolating the non-vertical movement from the tip member while transmitting to the tip member vertical movement through the pivot, so that the tip member moves through a vertical arc.

In further detail, the hinge resiliently bends about a vertical axis to isolate the lateral movement from the tip member.

In additional detail, the hinge resiliently twists about its axial axis to isolate the non-vertical movement from the tip member motion.

In additional detail, the hinge resiliently bends about a vertical axis to isolate the lateral movement from the tip member, and the hinge resiliently axially twists about its axial axis to isolate the non-vertical movement from the tip member motion.

In further detail, the drive mechanism defined above further includes a drive member for attachment to the drive shaft, the drive member defining a recess positioned offset to the drive shaft; the first end of the link member is a ball; and the recess forms a socket for snugly rotatingly and pivotingly receiving the ball.

In another aspect of the invention, the drive mechanism includes a link member having a first portion and a second portion, the first portion having a first end, and a second portion having a second end for receiving a tip member; a means for attaching the first end of the link member to the drive shaft in an off-center manner; a laterally-extending pivot axis formed between the first and second portions; and a resiliently flexible hinge portion having a vertical bending axis formed on the link member. When the drive shaft rotates, the first end of the link member is rotated off-center from the drive shaft, creating vertical, lateral, and a combination of vertical and lateral movement, and the hinge isolating the non-vertical movement from the tip member while transmitting to the tip member vertical movement through the pivot, so that the tip member moves through a vertical arc.

There are several different means for attaching, including a cam and cam-follower structure, a ball and socket structure, a pair of gears, a pair of opposing flexible hinges, each having a laterally extending flexing axis formed on a sub-frame, a slider and slide channel having a substantially vertical motion, and a track cam surface for engagement with the first end of the link member.

In another aspect of the invention, an attachment structure for attaching a tip member to a link member of an automatic flosser includes a latch tab formed on the link member; and a latch recess formed on the tip member. When the tip member is positioned on the link member, the latch tab engages the latch recess.

In further detail, the tip member has a cup-shaped portion with an open end and an interior wall; the latch recess includes a pair of recesses positioned on the inner wall; and the latch tabs includes a pair of tabs formed on the link member to engage the corresponding latch recesses when the tip member is positioned on the link member.

In further detail, a space is formed between the link member and the inner wall of the cup-shaped portion to allow the cup shaped portion to be resiliently converted from a substantially circular form to a substantially oval shape to disengage the latch tabs from the latch recesses and remove the tip member from the link member.

In additional detail to the attachment structure as described above, the attachment structure includes a primary and secondary keying structure. The primary keying structure requires the tip member to attach to the link member in any of two orientations, with the two orientations including the width of the blade extending vertically. The secondary keying structure requires the tip member to attach to the link member in one orientation, the one orientation including the blade if curving upwardly or downwardly.

In another aspect of the invention, a structure for removing a tip member from a link member of an interproximal flosser includes a slot for receiving the tip member, the slot having side walls that converge along the length of the slot to engage and deform the tip member as the tip member is moved along the slot.

The foregoing and other features, utilities and advantages of the invention will be apparent from the following more particular description of a preferred embodiment of the invention as illustrated in the accompanying drawings.

BRIEF DESCRIPTION OF THE DRAWINGS

FIG. 1 is a top view of a flossing device incorporating the drive mechanism of the present invention, showing the primary internal working parts in dash.

FIG. 2 is an enlarged section view taken along line 2—2 of FIG. 1, and shows the internal working parts, including the battery, D.C. motor, link member and tip member.

FIG. 3 shows an enlarged view of FIG. 2 with more detail.

FIG. 3A–I are section views taken along respective lines of FIG. 3.

FIG. 4, 4A, 4B, and 4C show top schematic views of the drive mechanism of the flosser of FIG. 1, with the eccentric drive member in different positions.

FIG. 4', 4A', 4B', and 4C' show the offset recess at various positions.

FIG. 5, 5A, 5B, and 5C show section views taken along respective lines in FIGS. 4, 4A, 4B, and 4C showing the drive mechanism in different positions.

FIG. 6 shows another embodiment of the drive mechanism.

FIGS. 6A, B, C1, C2, C3, and D are section views taken along respective lines of FIG. 6.

FIG. 7 shows another embodiment of the drive mechanism.

FIG. 8 shows another embodiment of the drive mechanism.

FIG. 9 shows another embodiment of the drive mechanism.

FIGS. 10A and B show another embodiment of the drive mechanism.

FIG. 13 shows another embodiment of the drive mechanism.

FIG. 14 shows an embodiment similar to that in FIG. 6, but with a more significant angle between the first and second portions of the link member.

FIG. 15 shows the tip member, including the tip cap, the flossing element, and the recess groove.

FIG. 16A and 16B show the first end of the link member for receiving the tip member, and shows the key structure.

FIGS. 19, 19A, 19A1 and 19B show a tip removal and storage structure having a tip removal slot.

FIG. 20 shows the tip member attaching to the end of the link member.

FIG. 22 shows a detail of the second embodiment of the tip removal slot.

DETAILED DESCRIPTION OF THE PREFERRED EMBODIMENT

Figure 3F:
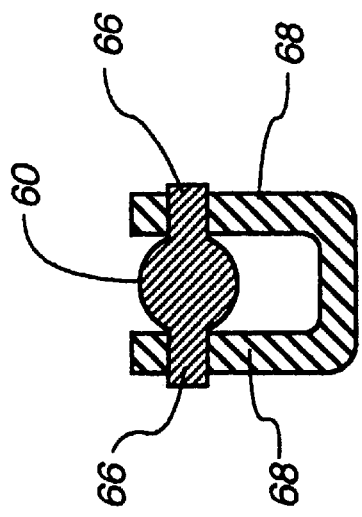
Figure 3I:
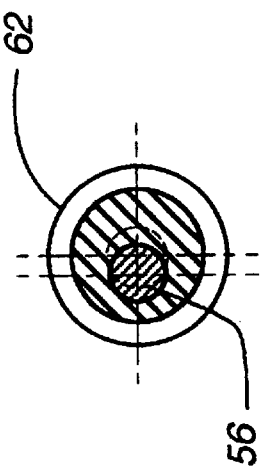
Figure 3E:
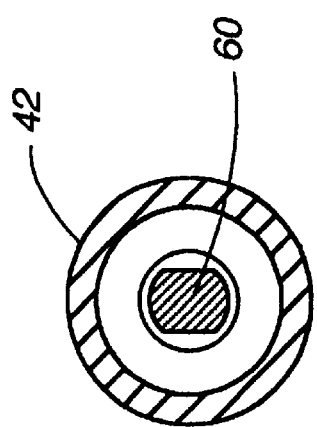
Figure 3H:
Figure 3D:
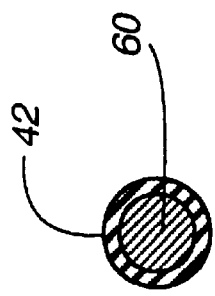
Figure 3G:
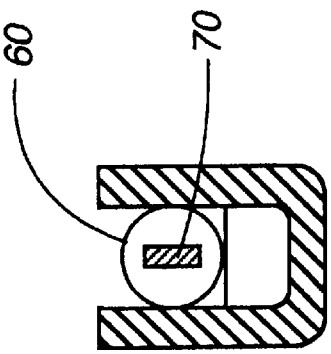

Referring first to FIGS. 1 and 2, an interproximal flosser 30 having the linear drive mechanism 32 of the present invention is shown. The interproximal flosser includes a housing 34 divided into two sections, a handle 36 in which the battery 38 and motor 40 reside, and a tip portion 42. The tip portion 42 of the housing 34 encloses the linear drive mechanism 32 as well as the on/off button 44. The tip portion 42 generally extends at an angle downwardly from the handle 36 to provide a desired handle/tip portion orientation for use. The motor 40 is a DC motor, known or available in the art, which includes a drive shaft 46 which is driven in rotation by the motor. The motor 40 is powered by a battery, such as a AA or AAA battery, which can be rechargeable as is known or available in the art. The motor shaft is attached to one end of the linear drive linkage 32 which extends inside the tip portion 42 to the terminal end of the tip portion of the housing, and extends therethrough to the outside of the tip portion 42. The exposed end of the drive linkage 32 receives a flossing member 48 through the use of a tip connection structure 50 described in detail below.

The linear drive linkage 32 converts orbital or rotational movement of the motor drive shaft 40 to linear movement at the flossing member 48. This is done by combining a horizontally-oriented pivot axis 52 with a vertically-oriented hinge (axis of bending is vertical), on the drive linkage 32, to effectively convert an orbital or rotational movement of the first end of the linkage into a linear movement at the second end 58 of the linkage. This linear movement is believed to be a more desirable flossing action than rotation (whether about the flossing member's axis or an axis offset therefrom).

In greater detail, the linear drive linkage 32 includes a single elongated link member 60 having a first end operably connected to the drive shaft 46 of the motor 40, and a second end 58 extending from the tip portion 42 of the handle 36 for receiving the tip or flossing member 48. The motor 40 is oriented in the handle 36 to generally rotate the drive shaft 46 about the longitudinal axis of the housing. The linear drive linkage 32 extends at an angle downwardly to follow the shape of the housing. See FIG. 2.

As shown in FIGS. 2 and 3, the first end of the link member 60 is attached to a drive member 62 (or offset connector), which is affixed to the shaft 46 of the motor 40 and rotates with the shaft of the motor. The outer end of the drive member 62 defines an off-center recess 64, for instance a circular hole, for receiving the first end of the link member 60. This offset recess 64 causes the first end to rotate around the shaft's 46 centerline (also characterized as moving in an orbital motion about the shaft's centerline) as the drive member 62 is rotated by the shaft 46. This rotating motion of the recess and first end of the link member 60 is generally concentric about the drive shaft 46.

The first end of the link member 60 can be of any reasonable shape for being received in the similarly-shaped off-center recess in the drive member 62. Preferably, the drive member 62 has a circular or spherical off-center recess 64 formed therein for receipt of the preferably substantially spherically-shaped first end of the link member 60. A ball and socket type of structure is contemplated. It is important that the first end of the link member 60 be tightly held in the recess 64 to minimize noise caused by the relative movement of the drive member and the first end of the link member 60 when the drive member 62 is rotated. Further, the friction between the first end of the link member 60 and the walls of the recess needs to be minimized to reduce wear and tear, and to reduce the energy consumption of the motor.

The link member 60 is divided into two portions, the first portion 63 associated with the first end and the second portion 65 associated with the second end 58. The two halves are generally delineated by a pivot 66. See FIGS. 2 and 3. The pivot 66 on the link member extends horizontally (laterally at right angles with the centerline of the flossing device) with respect to link member 60, and is restricted to allow pivotal movement in a vertical plane about a horizontal axis only. The pivot 66 is formed by two cylindrical protrusions, one extending from each side of the link member 60, each being rotatably received in a yoke 68 formed in the housing. The yoke 68 allows the protrusion to rotate therein about the horizontal pivot axis 52. These cylindrical protrusions are restrained in the yokes 68 to allow only rotation about the pivot axis 52. The yokes can be formed by cylindrical recesses formed in the housing or other like structure.

A flexible hinge 70 is formed in the link member 60 adjacent to the pivot 66 and in the first portion 63. The flexible hinge 70 has the full dimension of the height of the link member 60 in a vertical direction and is very thin relative to the height of the link member in the side-to-side direction (FIG. 2). The flexible hinge 70 is ideally a "living hinge" (made out of the same material as the rest of the link member 60, or can be a separate resilient member attached into the link member) 60. The flexible hinge 70 acts to allow the first section 63 of the link member 60 to bend laterally and twist axially when the first end of the link member 60 moves with the rotation of the off-center recess 64 in the drive member 62. The hinge 70 twists to absorb the lateral movement of the first end that is not purely horizontal. This lateral movement and twisting motion is thus isolated by the hinge so the second section 65 of the link member 60 moves only in a linear manner up and down about the pivot axis 52 of the pivot 66. It is believed that the hinge can be approximately 0.037 inches in thickness, 0.150 inches long, and 0.13 inches tall. The surrounding portion of the link member 60, before and after the hinge, is 0.1 inches thick, and 0.13 inches tall.

The hinge 70, which is flexible, preferably resiliently to automatically be biased back to its original position, in the side-to-side direction (in its thin dimension), and can twist, in combination with the fixed pivot, isolates the vertical motion from the generally rotary motion of the first section 63 of the link member 60. This vertical oscillating motion is transmitted to the second section 65 of the link member 60 to move the flossing tip 48 in a vertical, planar, reciprocating accurate motion.

When the first end of the link member 60 moves up and down as the off-center recess 64 in the drive member 62 moves from top to bottom during rotation, the hinge 70 bends laterally and twists axially, yet the larger (vertical) dimension of the hinge 70 is substantially rigid and thus transfers vertical motion through the pivot point to cause the pivot 66 to rotate or pivot along its horizontal axis This in turn causes the second end 58 of the link member 60 to move through a vertical arc with respect to FIG. 2 in a reciprocating, linear (or translatory) motion. The desired motion at the end of the tip member 48 is vertical, up-and-down movement in a single plane through an arc. This translatory motion is the desired motion for the tip 48 when cleaning the interproximal spaces between teeth.

The second end 58 of the link member 60 is free to move in the translatory motion inside the housing 34 and outside the housing such that when a tip member 48 is attached to the second end 58 of the link member 60 the tip member also moves in a translatory motion. The flexible hinge section 70 of the link member 60 acts as a living hinge to effectively absorb and isolate the side-to-side or lateral movement and twisting motion of the first end of the link member 60 and allows only the vertical up-and-down movement of the first end of the link member 60 to be transferred through the pivot 66 to the second end 58 of the link member 60 to cause the tip member 48 attached thereto to move up and down in a translatory linear oscillating motion defining an arc. This isolates the vertical movement components from the lateral movement components. The pivot restraint (yokes) 68 also isolates the lateral movement components from the vertical movement components.

Typical cam and follower structures, because of the clearance required, generate significant noise when the motor operates at approximately 9,000 rpm (the desired speed). To reduce this noise, the instant invention employs a ball-shaped first end of the link member 60 to be received in the off-center recess 64 (socket) of the drive member 62. The ball or spherical shape of the first end of the link member 60 can be more tightly toleranced with the off-center recess 64 in the drive member 62 to minimize the clearances and thereby reduce the noise level during operation. A ball and socket structure is shown in FIGS. 2 and 3.

FIGS. 4, 4A, 4B, 4C, 5, 5A, 5B, 5C schematically show the drive mechanism 32 of the present invention in four different positions to show how the flossing member 48 and second end 58 of the link member 60 move relative to the first end of the drive link member 60. FIGS. 4, 4A, 4B, and 4C show top views of the drive mechanism in four consecutive positions. FIGS. 5, 5A, 5B, and 5C are vertical section views to show the link member 60 and flossing member 48 position corresponding to FIGS. 4, 4A, 4B, and 4C, respectively.

Figure 4C:
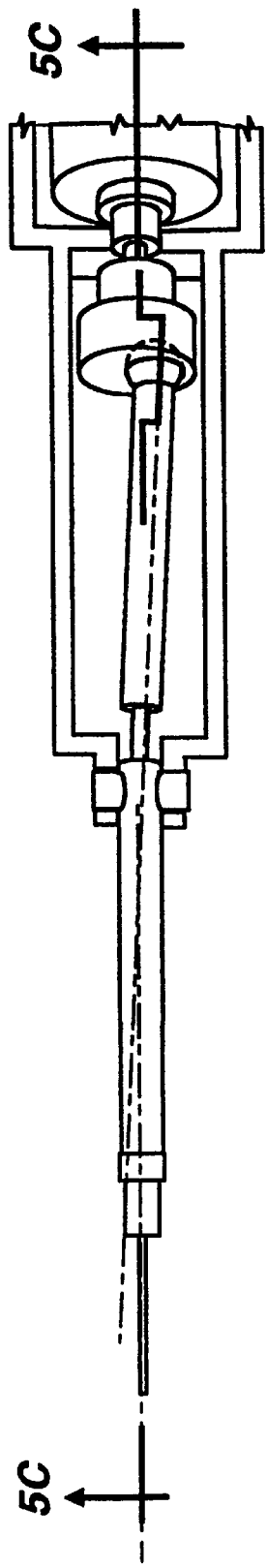
Figure 4C:

FIGS. 4 and 5 show the link member 60 with the drive member 62 in the top position (the offset recess pointing directly upwardly at 12 o'clock, as shown in FIG. 4'). This is the highest vertical offset position and the smallest lateral offset position the first end of the link member 60 is subject to above the centerline, and thus is the lowest position of the second end 58 of the link member 60 and the flossing member 48. In this position the hinge 70 is transferring all of the vertical motion of the first end of the link member 60 to the second end 58 of the link member 60 through the pivot 66. This position is represented by dashed line ww.

FIGS. 4A and 5A show the link member 60 with the drive member 62 in the left-most position (the offset recess pointing generally at 9 o'clock, as shown in FIG. 4A'). This is the smallest vertical offset position and the highest lateral offset position the first end of the link member 60 is subject to relative to the centerline, and thus is the intermediate position of the second end 58 of the link member 60 and the flossing member 48. In this position the hinge 70 is bending to absorb substantially all of the lateral motion of the first end of the link member 60, thus isolating the second end 58 of the link member 60 therefrom. The pivot 66 is not activated, and the link member 60 is thus in an intermediate or neutral position. This position is represented by dashed line xx.

FIGS. 4B and 5B show the link member 60 with the drive member 62 in the top position (the offset recess pointing directly downwardly at 6 o'clock, as shown in FIG. 4B'). This is the relatively lowest vertical offset position and smallest lateral offset position the first end of the link member 60 is subject to below the centerline, and thus is the highest position of the second end 58 of the link member 60 and the flossing member 48. In this position the hinge 70 is transferring all of the vertical motion of the first end of the link member 60 to the second end 58 of the link member 60 through the pivot 66. This position is represented by dashed line yy.

Figure 5C:
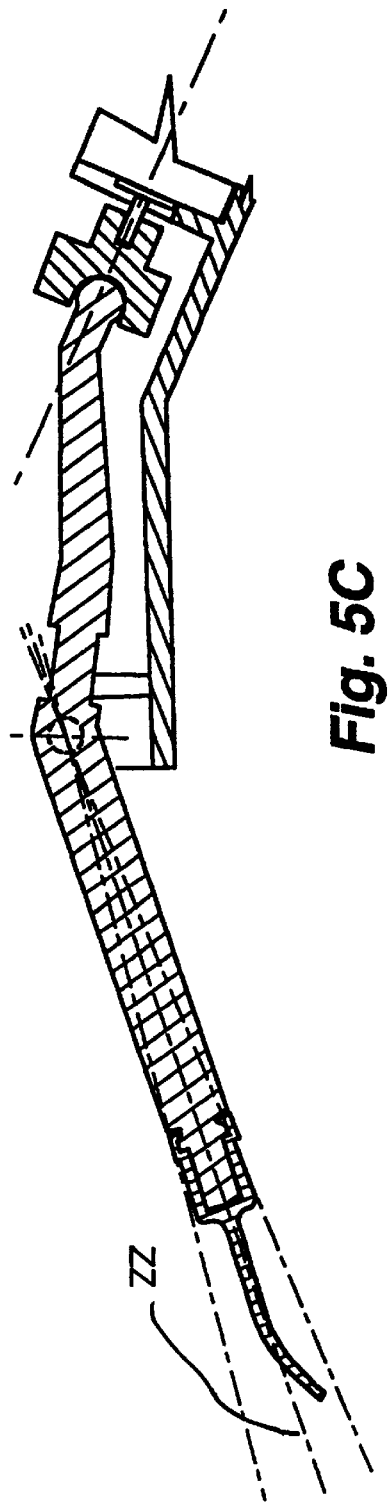

FIGS. 4C and 5C show the link member 60 with the drive member 62 in the right-most position (the offset recess pointing generally at 3 o'clock, as shown in FIG. 4C'). This is the smallest vertical offset position and the highest lateral offset position the first end of the link member 60 is subject to relative to the centerline (equal to the 9 o'clock position), and thus is the intermediate position of the second end 58 of the link member 60 and the flossing member 48. In this position the hinge 70 is bending to absorb substantially all of the lateral motion of the first end of the link member 60, thus isolating the second end 58 of the link member 60 therefrom. The pivot 66 is not activated, and the link member 60 is thus in an intermediate or neutral position. This position is represented by dashed line zz.

The stroke of the flossing member 48 is thus represented by the plane formed between dashed line ww and yy. Ideally, the motion of the tip of the flossing member 48 is approximately between 0.050 inches to 0.070 inches, at an angle of between 5 and 30 degrees (no angle required if entire flossing tip translates, as described below), and at a speed of 9,000 cycles per second. The flossing member 48 is moved through this stroke efficiently and with reduced noise.

The structure described above with respect to FIGS. 1, 2, 3, 4–4C, and 5–5C is a preferred embodiment for the present invention. It combines the desired noise level with the positioning of the pivot 66 and supporting yoke 68 to help the device have the desired size for ease of manipulation during use. If the pivot 66 is too close to the flossing member 48, the device would be more difficult to insert into a user's mouth. If the pivot 66 is too far away from the flossing member 48, the device would be longer than is necessary, and the link member 60 would need to be made larger to handle the moment loads. Nonetheless, a variety of different embodiments are possible for converting rotational movement to the preferred translatory movement. The similarity between all embodiments is that the link member 60 includes a hinge portion 70 and a fixed pivot 66 to isolate the vertical motion of the link member. Most of the differences described below address the engagement of the drive shaft 46 of the motor 40 to the first end 56 of the link member 60. Some of these other means for quietly and efficiently converting rotation into linear motion are described below.

FIG. 6 shows an embodiment where a flexible cable 80 is used to remotely position the connection of the link member 82 from the motor 40. This could be helpful if this connection was required to be offset from the motor for some reason. The cable 80 is attached at one end to the drive shaft 46, and at the other to an eccentric cam 84. A rotation bearing 86 supports the distal end of the cable and allows it to rotate with the drive shaft 46. The eccentric cam 84 can be used to drive a small link member 82 which includes a cam follower 88. The tip member (not shown) attaches to the end 90 of the small link member 82. The small link member has a pivot 92 to allow the link member to pivot about a fixed horizontal axis. The cam follower 88 is designed to follow the rotation of the eccentric in the vertical, up-and-down direction. The small link member 82 forms a living hinge 94, similar to the previous embodiment, to absorb (bend and twist) to isolate the lateral motion from the motion of the cam follower 88. This allows just the vertical motion to pass through the pivot 92 and cause the flossing member to pivot up and down through the desired planar arc, as shown.

FIGS. 6A shows a section of the small link member through the pivot protrusions and support yokes 96. FIG. 6B shows a section through the hinge section of the small link member. FIG. 6C1–6C3 show various positions of the cam follower 88 relative to the rotating drive shaft extension 80. FIG. 6C1 shows the cam follower 88 in its highest position. FIG. 6C2 shows the cam follower 88 at its largest lateral deviation, and FIG. 6C3 shows the cam follower 88 in its lowest position. FIG. 6D shows a section of the remote end of the drive shaft in the rotation bearing 86.

FIG. 7 shows a structure utilizing bevel gears 110. The small link member 112 and cam follower 114, as well as motor 40 are identical to that described above with respect to FIG. 6. The structure of FIG. 7 would allow for angular relation of the input to output, but would minimize the parasitic drag on the system existing in the structure of FIG. 6. This would have fewer complications than use of a universal joint, which could be used to replace the bevel gears 110 and would also work in this instance. The gear shafts and attachment ends could potentially be molded into one piece for each shaft. The eccentric 116 could be molded as a part of one of the shafts also. This design would require one or two rotational bearing features 118 for each shaft which could cause some parasitic drag. However, if the shaft with one of the gears of the eccentric was used to replace the existing eccentric 116 and the other shaft with its gears, and a mounting feature to the motor was used to replace the existing long rocker arm, there would be an equivalent number of parts. There may be gear noise as well as heat buildup at the gear faces, however, a potential advantage is that since this is a geared system the output speed (tip movement frequency) can be varied from the motor rotational speed. This may be beneficial in terms of cleaning effectiveness, motor selection, flexibility, and power requirements.

The cam-followers 88 and 116 of the structures of FIGS. 6 and 7 can be designed to only follow the eccentrics in the vertical up and down motion, not in the lateral direction. This would mean the link member would not have to include a flexible hinge portion to isolate the vertical motion.

FIG. 8 shows a DC motor 40 with the drive shaft 46 mounted directly to the eccentric 120. The small link member 122 and cam follower 124, as well as motor 40, are identical to that described above with respect to FIGS. 6 and 7. The small pivot arm 122 pivots about the pivot point 126, similar to structures of FIGS. 6 and 7. Again, because of the flexible hinge in the link member, the flossing member (not shown) follows only the vertical movement of the eccentric 120. In this embodiment, the motor is positioned very close to the flossing member.

FIG. 9 shows a structure similar to that of FIG. 8, except the tip 150 is attached directly to the off-center eccentric 152 mounted on the motor drive shaft 46, as opposed to a cam follower. The tip 150 combines both the tip member and the small pivot arm, and includes the pivot point 154 and the flexible hinge 156. The examples shown in FIGS. 8 and 9 rely on a DC motor being sufficiently small enough to fit in the tip portion of the housing. This option, depending on available space and motor capability, has a potential for the fewest number of drive mechanism components. With the redesigned combination tip 150, even the existing prototype mechanism could eliminate the small pivot arm. The biggest difference between the function of the redesigned tip designs is that the use of this tip with the existing long rocker arm design yields "single plane" oscillation, where use of the above-listed simplified design yields orbital motion unless special steps are taken, like constructing the tip beam that engages the eccentric so it flexes easily in the horizontal (lateral) direction but is very stiff in the vertical direction. Or, as described above with the various embodiments, the engagement between the tip 150 and the eccentric 152 could work to follow the cam (eccentric) in only the vertical movement and not the side-to-side or lateral movement.

Another option to obtain more pure "single plane" oscillation would be to create a "living flex" cantilever beam structure 160 utilizing a subframe 162 in the housing. This could take the eccentric rotational motion from the motor and turn it into "single plane" translatory oscillation. See FIGS. 10A and B. FIG. 10A shows a frame structure 162 having a living hinge 164 at the top and bottom areas to isolate the orbital movement of the eccentric 166 to cause simply linear motion in the vertical direction at the tip of the flossing member 168. The subframe is attached to an off-set drive shaft 168 for simplicity in explanation. The frame structure 164 is rigid in the lateral and other non-vertical directions, thus isolating those motions from the flossing member 168. The combination tip 168 would be similar to that shown in FIG. 9. FIG. 10B shows the frame 164 flexed upwardly, thus pushing the flossing member downwardly. The frame 164 would flex downwardly the same amount to generate the stroke as shown. In FIG. 10A, the frame is in the un-flexed position. This structure is basically a pair of opposing flexible hinges, each having a laterally extending flexing axis formed on a sub-frame. Another option related to this "living flex" concept would be to do away with the tip pivot and simply have a tip attached to the projection of the living flex element. This would enhance the "sealability" of the unit since the projection of the living flex element could be sealed to the main structure. However, depending on the space available, it may be necessary to position the motor and flex mechanism a significant (over 1.5 inches) distance away from the actual tip.

Figure 11:
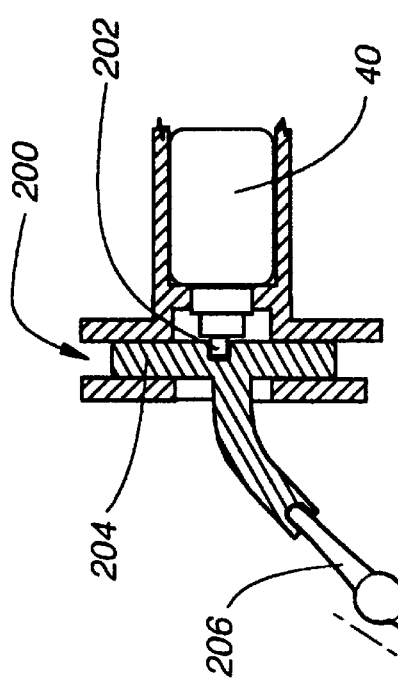
FIG. 11 shows another embodiment of the drive mechanism.

Another variation on this structure would be to replace the living flex portion of the mechanism with a slide channel 200 in the subframe of the housing, as shown in FIG. 11. This structure may require less force to move the tip holder since it is not flexing a member to create movement, but rather sliding a preferably low-friction free-flowing element. However, depending on the distance to the tip, a binding condition could exist in the slide channel contact area, which could degrade performance. In FIG. 11, the off-center cam 202 is attached to a slider 204, which is positioned in the slide channel 200, with the entire slider 204 moving up and down. Since the flossing element 206 is attached directly to the slider 204, the entire flossing tip moves up and down in pure translation, without any pivoting motion. See the outer dashed lines in FIG. 11 to show the approximate upper and lower positions. The angle of the flossing member 206 relative to the motor is easily adjustable by simply adjusting the angle at which the flossing member attaches to the slide member 204. This structure is basically a slider 204 and slide channel 200, the slide channel allowing only a substantially vertical movement of said slider.

Figure 12:
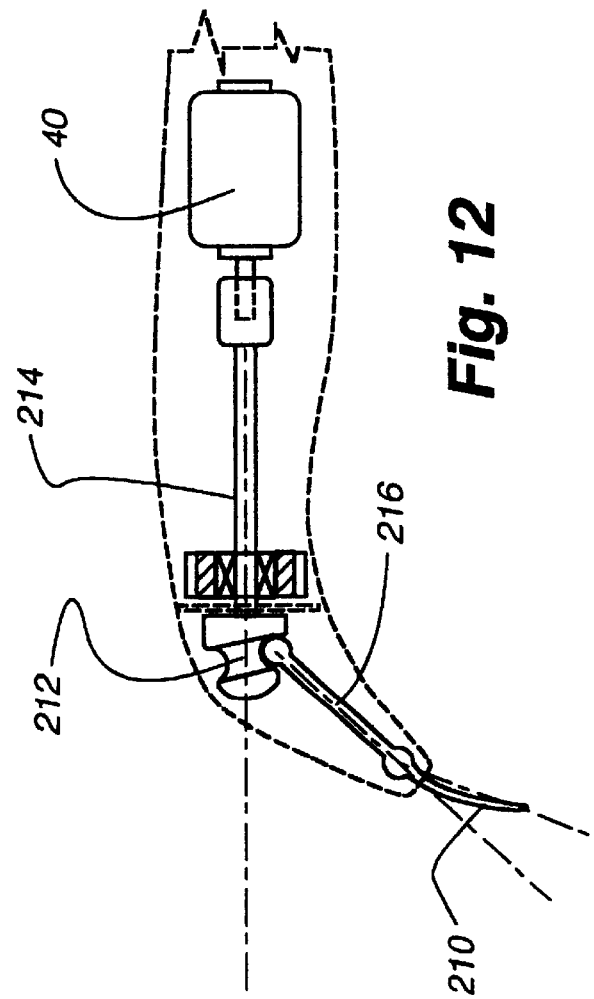
FIG. 12 shows another embodiment of the drive mechanism.

Another embodiment using pure rotary input motion with the motor 40 somewhat remote from the tip 210 would include a track cam 212 attached to the motor shaft 214 with the second end of the link member 216 engaging the track cam 212. See FIG. 12. The tip member 210 is pivotally mounted to the housing such that when the tip member 210 moves in the cam track 212 the external portion of the tip member 210 moves in a vertical arc, up and down. The first half of the link member 216 can be flexible to isolate the side-to-side movement as the first end is actuated by the track, and thus only pass the vertical movement through the pivot point. This structure reduces the drive system down to the motor and one fairly straightforward member (the rotating track cam element 212). The replaceable tip 210 is driven directly from the track cam 212. Since the motor bearings and bushings support the end of the track cam shaft, if the shaft needs to be long because of space constraints, then only one additional bearing surface should be required to constrain the shaft. However, if the space constraints allow the motor to be positioned close to the tip actuation point, then the motor bearings and bushings would be all that is required to support the shaft, because the shaft becomes very short. Also, this pure rotation should be much more in balance than the eccentric cam scheme of the prior art. With only the lightweight plastic flossing tip oscillating, the handle vibration should be reduced to a minimum. A seal could be positioned on this track cam shaft 212 as is known in the art, and the angled end portion of the device could be the color-coded, interchangeable nosepiece for different family members to use as contemplated.

FIG. 13 shows an alternative structure for attacking the link member 60 to the drive shaft 46. The drive shaft has an offset portion which is notably engaged in the first end 56 of the link member 60. The offset portion acts like the combination of the drive member 62 and recess 64 of the structure in the embodiment of FIGS. 1, 2 and 3.

FIG. 14 shows an alternative embodiment of the drive mechanism, similar to that of FIG. 7, with a more significant angle between the first and second portions of the link member 112'. Also, the cam follower 114' follows a camming device 116', which is attached to a drive member 115, which is in turn attached to the drive shaft 46. This structure allows a direct attachment of the link member to the motor. The offset angle formed between the portions of the link member, delineated by the pivot, allow for different relative positions of the flossing member with respect to the motor.

The linear drive linkage of the present invention efficiently converts pure rotary motion to oscillating translatory motion (pivotal up and down movement through a vertical plane) for effective flossing action in the interproximal gaps between one's teeth. The structures described herein minimize or eliminate any side to side movement of the tip member by isolating the up and down movement from the lateral movements through the drive structure between the rocker arm and the motor drive shaft. Preferably, a combination horizontal pivot and vertically oriented flexible section of the rocker arm are used in combination to isolate the up and down vertical motion and eliminate the side to side or lateral motion.

The second end of the link member is designed to receive the tip member. Preferably, the tip member is both securely attached to the second end of the link member, yet can be easily released therefrom for replacement. FIG. 15 shows the structure of the tip member. The tip member 250 generally includes a tip cap 252 from which extends the flossing element 254. The flossing element 254 and tip cap 252 are made of plastic. The flossing element 254 extends from the center of the end of the tip cap 252 and can be straight, curved or a combination of both. The flossing element 254 is sized to be received in the interproximal spaces. The tip cap 252 has a cup-like shape forming a cavity with a closed end 256 from which the flossing element extends and an open end 258 which receives the second end of the link member. Adjacent the open end 258, an annular groove 260 is formed on the interior wall 262 of the tip cap 252.

Adjacent the closed end 256 of the tip cap a keying feature 264 is formed on the lower side walls thereof. See FIG. 15. The keying feature 264 can be an angled plane or the like as described in greater detail below. The tip cap 252 is typically generally cylindrical, but can be deformed to an oval shape as described below. Also, the annular groove 260 does not have to extend around the circumference of the interior of the tip cap at a location adjacent the open end, but instead can be diametrically opposed recesses, for instance at the top and bottom as shown in FIG. 15. The purpose of the latching recess will be described in greater detail below.

Figure 17D:
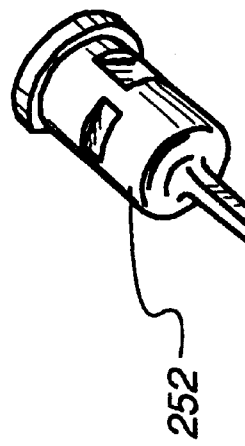
FIGS. 17A–D show the tip member without the secondary key structure, and the connection structure for attachment to the link member.
Figure 17C:
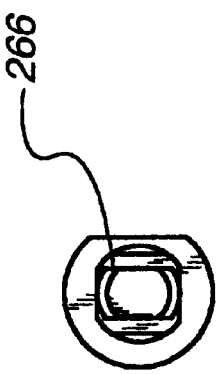
Figure 17B:
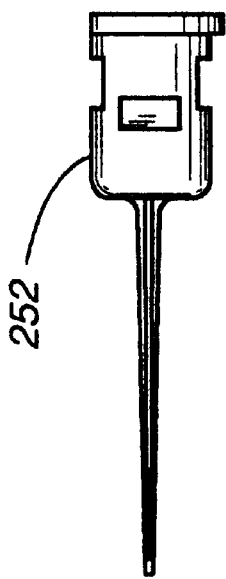
Figure 17A:
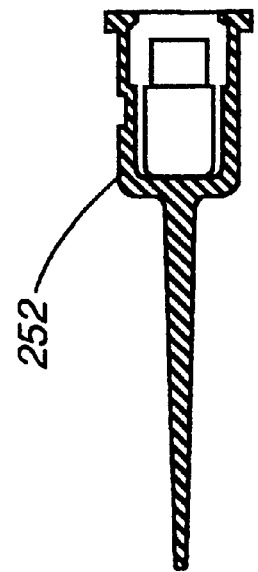
Figure 17F:
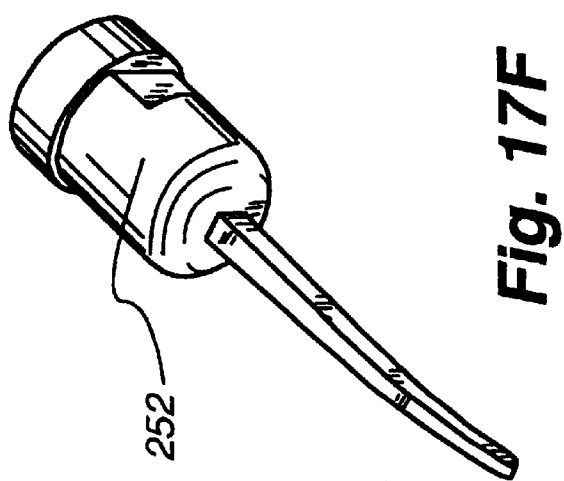
FIGS. 17E–H show another embodiment of the tip member and the connection structure for attachment to the link member.
Figure 17G:

FIGS. 17A, B, C and D also show the tip member. Here there is no secondary keying feature, just a rectangular aperture 266 allowing the tip to be mounted one of two ways on the end of the link member. This is appropriate where the flossing member is straight and thus there is no up or down orientation. The tip material is preferably Dupont Zytel 101L, or the like, such as NC010 (nylon 66).

FIGS. 16A and 16B show a preferred structure of the second end 270 of the link member 272. Link member 272 is similar to link member 60 described above, and can be used in any embodiment described herein. The second end of the link member is sized to fit within the tip cap of FIG. 15, and includes diametrically opposed latch tabs 274 that snap into the latching recess when the second end of the link member is inserted into the tip cap 252. A keying structure 276 is incorporated into the second end to mate with the keying structure 264 of the tip. The key structure can have a primary key and a secondary key. The primary key is needed regardless of whether the tip is curved or straight, and insures that the tip is mounted so that it vibrates along the skinny axis of the blade so it fits appropriately between the user's teeth. The primary key simply helps insure that the end of the link member is rectangular and only accepts the tip in two corresponding orientations.

The secondary key is necessary where the tip is curved and thus has a proper up and down orientation. A preferred keying feature 276 is defined near the second end 270 of the link member 272 to mate with the secondary keying feature 264 inside the tip cap 252. This secondary keying feature allows the tip cap 252 to be positioned in only one orientation on the second end of the link member in the event the flossing element is curved and requires a particular orientation for proper use. The secondary keying feature is not required unless the particular orientation of the tip cap 252, when mounted on the second end of the link member, is desired. Other types of secondary keying features can be used, including other geometrical shapes, notches and grooves, or the like, to allow an engagement of the keying features for insertion of the second end of the link member into the tip cap. The preferred secondary keying feature described herein is preferred because of its ease of manufacture and simplicity.

A sealing surface 280 is defined on the second end 270 of the link member 272 spaced away from the latch tabs 274 and on the side of the latch tabs away from the free end of the link member. The rim of the tip cap 252 engages the sealing surface 280 (which can be an annular boss formed around the link member).

FIGS. 18A–E shows an alternative embodiment of the second end of the link member not requiring a keying feature. The link member is similar to that shown in FIGS. 1, 2 and 3.

Figure 17E:
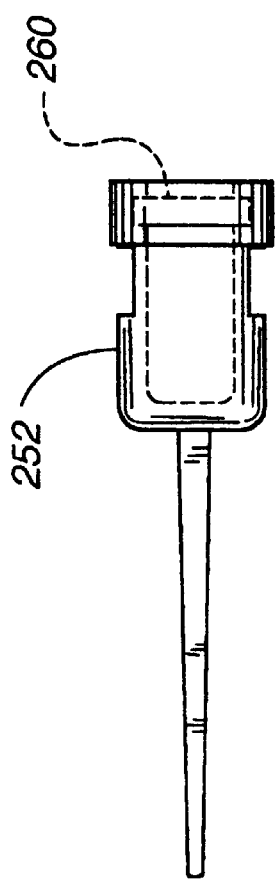
Figure 17H:
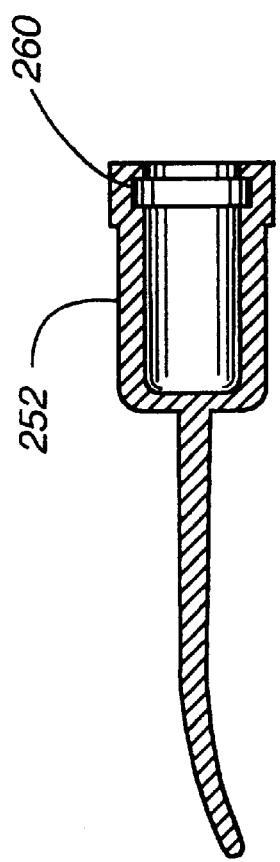
Figure 18D:
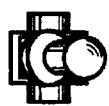
FIGS. 18A–E show the link member, including the latch tabs.
Figure 18E:
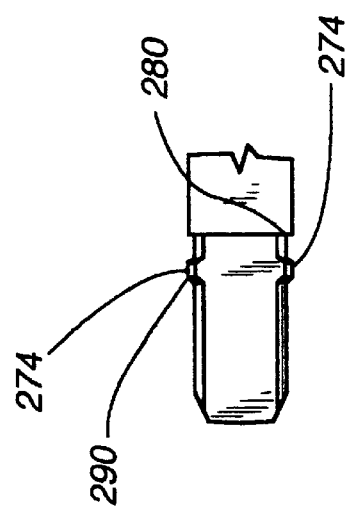
Figure 18C:
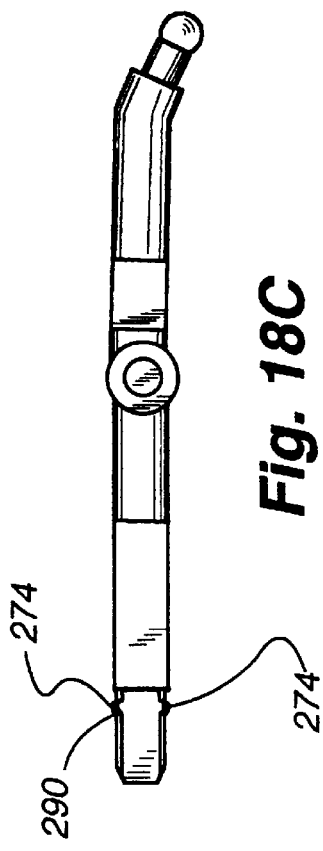
Figure 18B:
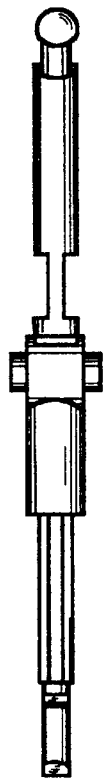
Figure 18A:
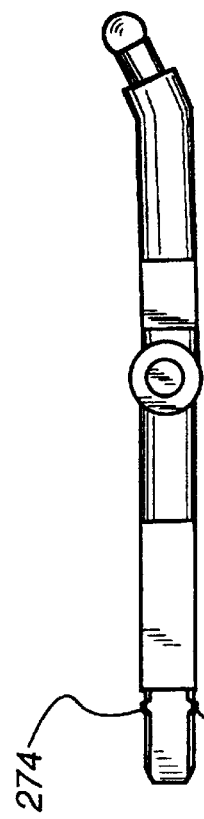

FIGS. 17E, F, G and H show an embodiment of the tip cap 252 and flossing element 254. The external surface of the tip cap 252 adjacent the rim defines opposed notches. The primary and secondary keying structures are combined in this structure by having a pie-shaped opening in the tip cap to receive a correspondingly-shaped second end of the link member.

In operation the enclosed latching recess 260 in the tip cap 252 engages the latching tabs 272 on the mechanism (the second end of the link member) to hold the tip in place. The keying feature prevents the tip from being installed in the improper orientation if that feature is desired. The tip is disengaged from the second end of the link member by compressing the sides of the tip cap 252 to deform it into essentially an elliptical shape. This would create a major axis of an ellipse which would be larger than the distance across the latching tabs 272 on the second end of the link member. The tip could then be easily removed because the latch tabs disengage from the latch grooves when the sidewalls are squeezed.

A tip-holding cartridge could provide the compression means for insertion or removal without the user having to directly contact the tip. There is a gap formed on either side of the second end of the link member when inserted in the tip cap to allow the tip cap to be squeezed to form an elliptical shape. The tip cap can deformed to an ovalized or non-circular shape to release the latch tabs 272 from the latch recesses 260.

This detent-style tip connection allows for secure placement of the tip member on the second end of the link member yet also allows for convenient removal of the tip member from the second end of the link member. When the tip member is positioned on the second end of the link member, an audible "click" is heard when the tip member is correctly seated thereon. This is a positive feature for assuring the user that the tip member is firmly attached to the device.

The latch tabs 274 can have at least a sloped front surface 290 (see FIG. 18E) to allow for a sliding engagement of the tip cap 252 over the second end of the link member so that the tip cap 252 is gradually increased in size to allow the latch tabs 274 to seat in the latching recess 260. The tip cap 252 is sufficiently resilient to rebound to its circular shape to cause the latch tabs 274 to be received in the latch recesses 260 and thus hold the tip on the second end of the link member.

The tip can be removed from the second end of the link member by squeezing the sides of the tip that are offset approximately 90 degrees from the engagement of the latch members 274 with the latch recesses 260 in the tip cap 252. Compressing the tip cap 252 at this location causes the tip cap to form an elliptical or oval shape, disengaging the latch tabs from the latch recesses 260 and allows the tip cap 252 to be removed from the device. This can be done by hand, with a tool, such as pliers, or by the tip removal device shown in FIGS. 19, 21, and 22.

FIG. 19 shows a flosser tip cartridge 300 including several replacement flosser tip members 302 positioned circumferentially around the outer rim of the top cap, and a specially formed slot 304 formed across the center of the top cap. Once the flosser tip 250 is attached to the second end of the link member, as is shown in FIG. 20, the flosser tip is releasably attached thereto. To remove the flosser tip from the second end of the link member, the flosser tip 250 is inserted into the slot 304 at the first end 306, as shown in arrows of FIG. 19B, and then moved along the slot 304 to compress the opposing sides of the tip cap 252 and release the latch tabs 274 to allow the tip 250 to fall into the reservoir 300 for easy collection and disposal.

The first end 306 of the slot 304 has a substantially circular shape to allow the insertion of the tip 250 therethrough. The upper edges 308 of the slot 304 slope outwardly at the first end 306 and gradually transition to a vertical orientation about half way between the first end 306 and the second end 310 of the slot. The seal collar 280 (FIG. 15) formed around the second end of the link member rests on the top edge of the slot 304 and as the tip 250 is moved along the slot, the sides are compressed by the side walls of the slot 304 to cause the tip cap 252 to be deformed into an elliptical shape to allow the latch tabs 274 to be released from the latch recesses 260. See FIG. 19A1 for another representation of the slot shown in FIGS. 19A and B. The sides of the slot 304 preferably engage the opposing notches on the sides of the tip cap 252. At the second end 310 of the slot 304, when the flossing device is pulled upwardly from the slot 304, the tip 250 is held in the slot 304 such that it is removed from the second end of the link member.

Figure 21A:
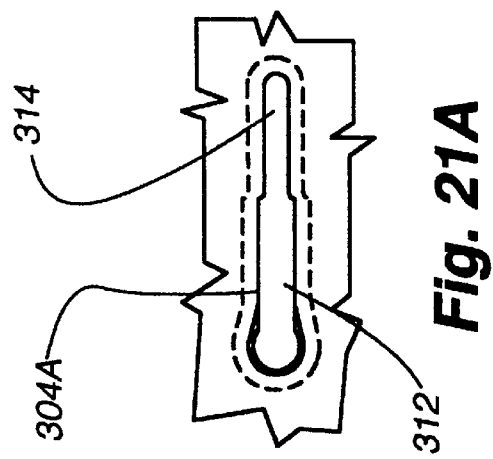
FIGS. 21A, 21B and 21C show another embodiment of the tip removal slot.
Figure 21B:
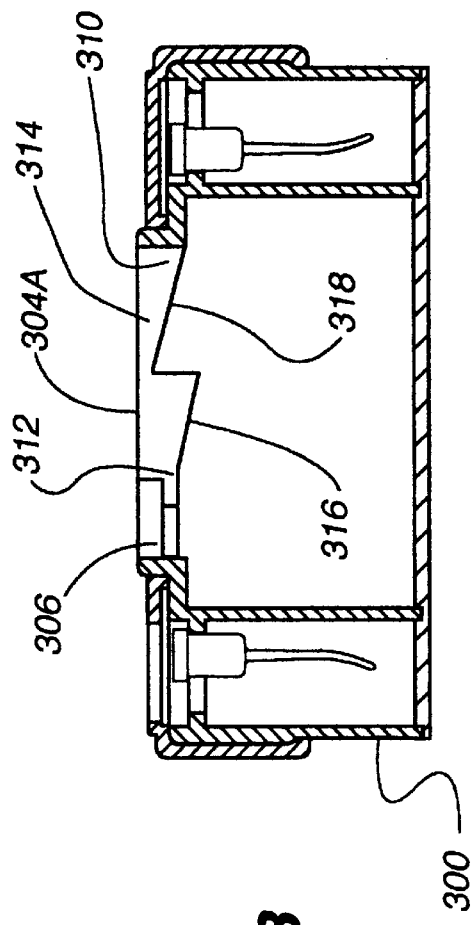
Figure 21C:
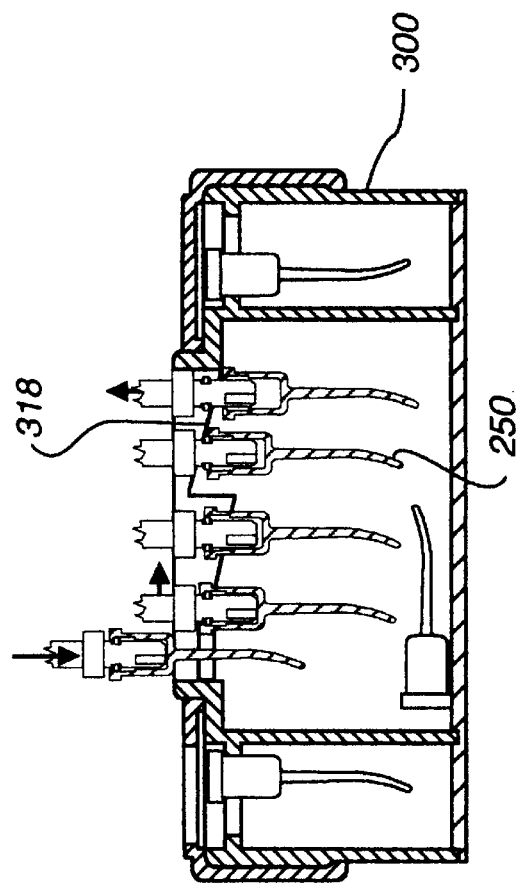

FIGS. 21A, B and C show another embodiment of this tip removal device where the slot 304A is broken into at least two sections: one section 312 being similar to that shown in FIGS. 19A and B where the tip is deformed into an elliptical shape such that the latch tabs 274 are released from the latch recesses 260 in the tip, and a second section 314 where the tip 250 is forcibly removed and ejected from the second end of the link member without having to remove the second end of the link member from the slot 304. This structure entirely removes the flosser tip 250 from the second end of the link member and ejects it into the receptacle cavity. The first end 306 of this slot 304A in FIG. 21A is for receiving the flosser tip 250. As the flosser tip 250 is moved along the slot 304A, a first downwardly sloped surface 316 (FIG. 21B) on either side of the slot 304A engages the sides of the flosser tip 250 to compress the flosser tip 250 into an elliptical shape and release the latch mechanisms to allow the flosser tip to be slid towards the end of the second end of the link member. The sidewalls preferably engage the opposing notches on the tip cap 252, and push the tip cap along the second end of the link member by moving down the ramp as the cap is moved along the first section of the slot.

At the second section 314 of the slot 304A, a second downwardly sloping ramp 318 (FIG. 21B), offset upwardly from the first downwardly sloping ramp, is formed on either side of the slot 304A and engages the top side of the rim of the tip cap 252 to further force the flosser tip 250 all the way off the second end of the link member as the device is moved to the second end of the slot. See FIG. 21C.

FIG. 22 shows an enlarged view of the slot 304A structure in cross-section. Again, the slot ramp 316 acts to compress the tip cap 252 to cause it to form an elliptical shape to disengage the latch tabs 274 and push the flosser tip 250 partially from the second end of the link member. The final ejection ramp 318 in the second section 314 of the slot engages the rim of the flosser tip to finally push the entire flosser tip off the second end of the link member as the device is moved to the second end 310 of the slot 304A. Using the slot to compress the tip 250 and release the latch tabs 274, additional features were added to eject the tip from the end of the device and are summarized here. The tip 250 is inserted into the release slot 304A. As the tip 250 is slid along the slot 304A and compressed to release the latch tabs 274, it is also guided down the slot ramp 316. This pulls the tip 250 down and off the attachment end of the device. As the tip 250 clears the end of the slot ramp 316, the very end (the rim) of the tip cap 252 contacts the final ejection ramp 318 and is pushed clear of the tip attachment end of the device (see FIG. 21C also).

The automatic removal of the flosser tip from the end of the device is a convenience to allow the user to easily replace the tips by sliding the second end of the link member along the slot, removing the tip member and easily replacing the tip by simply inserting it into a new flosser tip stored adjacent to the slot.

While the invention has been particularly shown and described with reference to a preferred embodiment thereof, it will be understood by those skilled in the art that various other changes in the form and details may be made without departing from the spirit and scope of the invention.

We claim:

1. A drive mechanism for an interproximal flosser having an electric motor with a rotating drive shaft, the drive mechanism comprising:

a link member having a first portion and a second portion, said first portion having a first end for attachment to said drive shaft in an off-center manner, and a second portion having a second end for receiving a tip member;

a laterally-extending pivot axis formed on said link member; and a flexible hinge portion having a vertical bending axis formed on said link member;

wherein when the drive shaft rotates, said first end of said link member is rotated off-center from said drive shaft, creating vertical, lateral, and a combination of vertical and lateral movement, and said flexible hinge portion isolating said lateral movement from said tip member while transmitting to said tip member said vertical movement through said pivot axis, so that said tip member moves through a vertical arc; and wherein said flexible hinge portion resiliently twists about its axial axis to isolate said lateral movement from said tip member motion.

2. A drive mechanism for an interproximal flosser having an electric motor with a rotating drive shaft, the drive mechanism comprising:

a link member having a first portion and a second portion, said first portion having a first end for attachment to said drive shaft in an off-center manner, and a second portion having a second end for receiving a tip member;

a laterally-extending pivot axis formed on said link member; and a flexible hinge portion having a vertical bending axis formed on said link member;

wherein when the drive shaft rotates, said first end of said link member is rotated off-center from said drive shaft, creating vertical, lateral, and a combination of vertical and lateral movement, and said flexible hinge portion isolating said lateral movement from said tip member while transmitting to said tip member said vertical movement through said pivot axis, so that said tip member moves through a vertical arc; and wherein said flexible hinge portion resiliently bends about a vertical axis to isolate said lateral movement from said tip member, and said flexible hinge portion resiliently axially twists about its axial axis to isolate said lateral movement from said tip member motion.

3. A drive mechanism for an interproximal flosser having an electric motor with a rotating drive shaft, the drive mechanism comprising:

a link member having a first portion and a second portion, said first portion having a first end for attachment to said drive shaft in an off-center manner, and a second portion having a second end for receiving a tip member;

a laterally-extending pivot axis formed on said link member; and a flexible hinge portion having a vertical bending axis formed on said link member;

wherein when the drive shaft rotates, said first end of said link member is rotated off-center from said drive shaft, creating vertical, lateral, and a combination of vertical and lateral movement, and said flexible hinge portion isolating said lateral movement from said tip member while transmitting to said tip member said vertical movement through said pivot axis, so that said tip member moves through a vertical arc; and wherein said flexible hinge portion is a living hinge made of the same material as said first and second portions of said link member.

4. A drive mechanism for an interproximal flosser having an electric motor with a rotating drive shaft, the drive mechanism comprising:

a link member having a first portion and a second portion, said first portion having a first end, and a second portion having a second end for receiving a tip member;

a means for attaching said first end of said link member to the drive shaft in an off-center manner;

a laterally-extending pivot axis formed between said first and second portions; and a flexible hinge portion having a vertical bending axis formed on said link member;

wherein when the drive shaft rotates, said first end of said link member is rotated off-center from said drive shaft, creating vertical, lateral, and a combination of vertical and lateral movement, and said flexible hinge portion isolating said lateral movement from said tip member while transmitting to said tip member said vertical movement through said pivot axis, so that said tip member moves through a vertical arc; and wherein said means for attaching includes a pair of opposing flexible hinges, each having a laterally extending flexing axis formed on a sub-frame.

* * * * *